United States Patent [19]

Walter

[11] Patent Number: 5,446,040
[45] Date of Patent: Aug. 29, 1995

[54] PESTICIDES

[75] Inventor: Harald Walter, Basel, Switzerland

[73] Assignee: Ciba-Geigy Corporation, Ardsley, N.Y.

[21] Appl. No.: 159,029

[22] Filed: Nov. 29, 1993

Related U.S. Application Data

[62] Division of Ser. No. 10,972, Jan. 29, 1993, abandoned.

[30] Foreign Application Priority Data

Feb. 7, 1992 [CH] Switzerland .......................... 376/92

[51] Int. Cl.$^6$ .................... C07D 401/12; A01N 43/54
[52] U.S. Cl. .................... 514/213; 514/269; 514/274; 514/256; 540/593; 544/319; 544/310; 544/317; 544/322; 544/327; 544/328
[58] Field of Search ............... 514/269, 274, 256, 213; 540/593; 544/319, 310, 317, 322, 327, 328

[56] References Cited

U.S. PATENT DOCUMENTS

| | | | |
|---|---|---|---|
| 3,821,228 | 6/1974 | Richards | 260/288 |
| 4,100,278 | 7/1978 | Nedelec et al. | 424/244 |

FOREIGN PATENT DOCUMENTS

| | | |
|---|---|---|
| 0057440 | 8/1982 | European Pat. Off. |
| 0264217 | 4/1988 | European Pat. Off. |
| 0323757 | 7/1989 | European Pat. Off. |
| 0326329 | 8/1989 | European Pat. Off. |
| 0370704 | 5/1990 | European Pat. Off. |
| 0424125 | 4/1991 | European Pat. Off. |
| 92/08704 | 5/1992 | WIPO . |

OTHER PUBLICATIONS

Chem. Abst. 113:78243c, Jones et al. (1990).
Chem Abst 89:163368c, Vasil'eva et al. (1978).
Chem Abst 81:120498n, Richards (1974).
Chem Abst 76:41827n, Baxter et al. (1972).
Chem Abst 71:30369k, Richards (1969).
Chem Abst 70:3950r, Wright (1969).
Chem Abst 69:106505h, Kotler-Brajtburg (1968).
Chem Abst 65:15358q, Kametani et al. (1966).
Chem Abst 63:4292f, Kametani et al (1965).
Chem Abst 115:282072s, Eckstein (1991).
Chem Abst 103:510m, Huff et al (1985).
Chem Abst 63:4293a, Kametani et al (1965).
Chem Abst vol. 79, No. 31921m Phizer Corp (1973).

*Primary Examiner*—John M. Ford
*Attorney, Agent, or Firm*—Marla J. Mathias

[57] ABSTRACT

Compounds of the formula

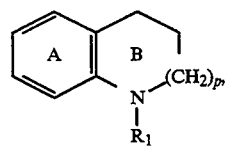

(I)

wherein the variables $R_1$ and p and the rings A and B are as defined in claim 1, and, where appropriate, tautomers thereof, in each case in free form or in the form of a salt, can be used as agrochemical active ingredients and can be prepared in a manner known per se.

13 Claims, No Drawings

PESTICIDES

This is a divisional of Ser. No. 08/010,972, filed Jan. 29, 1993, now abandoned.

The invention relates to compounds of the formula

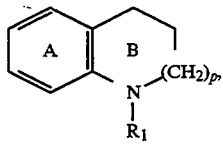

wherein one of the (p+6) substitutable flag carbon atoms of the two rings A and B is substituted by a group of formula Ia

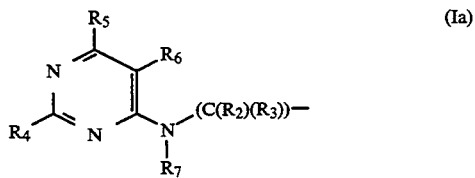

and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, any substituents present at the mentioned (p+5) substitutable ring carbon atoms of the two rings A and B being selected from the group consisting of halogen, $C_1-C_8$alkyl, halo-$C_1-C_8$alkyl, $C_1-C_4$alkoxy-$C_1-C_4$alkyl, $C_3-C_8$cycloalkyl, $C_1-C_8$alkoxy, halo-$C_1-C_8$alkoxy, $C_3-C_8$cycloalkoxy, $C_1-C_8$alkylthio, halo-$C_1-C_8$alkylthio, cyano, nitro, phenyl, phenoxy and phenylthio, the phenyl groups in phenyl, phenoxy and phenylthio being unsubstituted or substituted by one, two or three substituents selected from the group consisting of halogen, $C_1-C_4$alkyl and $C_1-C_4$lkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

$R_1$ is hydrogen, $C_1-C_8$alkyl, $C_3-C_8$cycloalkyl, benzyl, $C_1-C_8$alkanoyl that is unsubstituted or substituted by halogen or by $C_1-C_4$alkoxy, benzoyl the phenyl group of which is unsubstituted or substituted by one or two substituents selected from the group consisting of halogen, $C_1-C_4$alkyl, nitro and cyano; $C_1-C_8$alkanesulfonyl, halo-$C_1-C_8$alkanesulfonyl, cyano-$C_1-C_8$alkanesulfonyl or phenylsulfonyl the phenyl group of which is unsubstituted or substituted by one or two substituents selected from the group consisting of halogen, $C_1-C_4$alkyl, nitro and cyano;

$R_2$ and $R_3$, independently of one another, are hydrogen, $C_1-C_8$alkyl, halo-$C_1-C_8$alkyl, $C_1-C_4$alkoxy-$C_1-C_4$alkyl or $C_3-C_8$cycloalkyl;

$R_4$ is hydrogen, $C_1-C_8$alkyl, $C_1-C_8$alkoxy or $C_1-C_8$alkylthio;

$R_5$ is hydrogen, $C_1-C_8$alkyl, halo-$C_1-C_8$alkyl, $C_1-C_4$alkoxy-$C_1-C_4$alkyl, $C_1-C_4$alkylthio-$C_1-C_4$alkyl, $C_1-C_4$alkanesulfinyl-$C_1-C_4$alkyl, $C_1-C_4$alkanesulfonyl-$C_1-C_4$alkyl, $C_2-C_8$alkenyl, halo-$C_2-C_8$alkenyl, $C_{21}-C_8$alkynyl, $C_3-C_8$cycloalkyl, $C_1-C_8$alkylthio or halogen;

$R_6$ is hydrogen, hydroxy, $C_1-C_8$alkyl, halo-$C_1-C_8$alkyl, $C_1-C_4$alkoxy-$C_1-C_4$alkyl, $C_1-C_8$alkoxy, $C_1-C_8$alkylthio, $C_1-C_8$alkanesulfinyl, $C_1-C_8$alkanesulfonyl, halogen, nitro, cyano, amino, a group of the formula $N(H)R_8$(Ib), a group of the formula $N(R_8)R_9$(Ic) or a group of the formula $N=C(R_9)R_{10}$(Id);

$R_7$ is hydrogen, $C_1-C_8$alkyl, benzyl, $C_1-C_8$alkanoyl, phenylcarbonyl the phenyl group of which is unsubstituted or substituted by one, two or three substituents selected from the group consisting of halogen and $C_1-C_4$alkyl; $C_1-C_8$alkylthio, halo-$C_1-C_8$alkylthio, cyano-$C_1-C_8$alkylthio, phenylthio or benzylthio, the phenyl groups in phenylthio and benzylthio being unsubstituted or substituted by one or two substituents selected from the group consisting of halogen, $C_1-C_4$alkyl, nitro and cyano;

$R_8$ is $C_1-C_8$alkyl, benzyl, $C_1-C_8$alkanoyl, phenylcarbonyl the phenyl group of which is unsubstituted or substituted by one, two or three substituents selected from the group consisting of halogen and $C_1-C_4$alkyl; $C_1-C_8$alkylthio, halo-$C_1-C_8$alkylthio, cyano-$C_1-C_8$alkylthio, phenylthio or benzylthio, the phenyl groups in phenylthio and benzylthio being unsubstituted or substituted by one or two substituents selected from the group consisting of halogen, $C_1-C_4$alkyl, nitro and cyano;

$R_9$ is $C_1-C_8$alkyl;

$R_{10}$ is hydrogen or $C_1-C_8$alkyl; and p is 1 or 2;

and, where appropriate, to tautomers thereof, in each case in free form or in the form of a salt, to a process for the preparation of and to the use of those compounds and tautomers, to pesticides the active ingredient of which is selected from those compounds and tautomers, in each case in free form or in the form of an agrochemically acceptable salt, to a process for the preparation of and to the use of those compositions and to intermediates for the preparation of the compounds of formula I and of their tautomers.

The compounds I may in some cases be in the form of tautomers. If, for example, the radical $R_6$ in the group Ia is hydroxy, corresponding compounds may be in equilibrium with the tautomeric oxo derivatives, i.e. the corresponding pyrimid-5-ones. Accordingly, hereinafter, compounds I may be understood where appropriate as being also corresponding tautomers, even if the latter are not mentioned specifically in each case.

The compounds I and, where appropriate, the tautomers thereof may be in the form of salts. Since the compounds I have at least one basic centre, they are capable, for example, of forming acid addition salts. Those salts are formed, for example, with strong inorganic acids, such as mineral acids, for example sulfuric acid, a phosphoric acid or a hydrohalic acid, with strong organic carboxylic acids, such as unsubstituted or halosubstituted $C_1-C_4$alkanecarboxylic acids, for example acetic acid, unsaturated or saturated dicarboxylic acids, for example oxalic, malonic, maleic, fumaric or phthalic acid, hydroxycarboxylic acids, for example ascorbic, lactic, malic, tartaric or citric acid, or benzoic acid, or with organic sulfonic acids, such as unsubstituted or halo-substituted $C_1-C_4$alkane- or aryl-sulfonic acids, for example methane- or p-toluene-sulfonic acid. In addition, compounds I having at least one acid group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine. It is also possible where appropriate for corresponding internal salts to be formed. Preference is given within the scope of the invention to agrochemically advantageous salts; also included, however, are salts that have disadvantages for agrochemical uses, for example salts that are toxic to bees or to fish; those salts are used, for example, for the isolation or purification of free compounds I or the agrochemically acceptable salts thereof. Owing to the close relationship between the compounds I in free form and in the form of their salts, hereinbefore and hereinafter the free compounds I and their salts should be understood as meaning also the corresponding salts or the free compounds I, respectively, where appropriate and expedient. The same applies to tautomers of compounds I and their salts.

Unless otherwise defined, the general terms used hereinbefore and hereinafter have the meanings given below.

Halogen—as a group per se and as a structural element of other groups and compounds, such as haloalkyl, haloalkenyl, haloalkoxy, haloalkylthio and haloalkanesulfonyl—is fluorine, chlorine, bromine or iodine, especially fluorine, chlorine or bromine.

Unless otherwise defined, groups and compounds that contain carbon each contain from 1 up to and including 8, preferably from 1 up to and including 4, especially 1 or 2, carbon atoms.

Alkyl—as a group per se and as a structural element of other groups and compounds, such as haloalkyl, alkoxy, haloalkoxy, alkoxyalkyl, alkylthio, cyanoalkylthio, haloalkylthio, alkylthioalkyl, alkanesulfinyl, alkanesulfinylalkyl, alkanesulfonyl, cyanoalkanesulfonyl, haloalkanesulfonyl and alkanesulfonylalkyl—in each case taking due account of the number of carbon atoms respectively contained in the corresponding group or compound, is either straight-chain, i.e. methyl, ethyl, propyl, butyl, pentyl, hexyl, heptyl or octyl, or branched, e.g. isopropyl, isobutyl, sec-butyl, tert-butyl, isopentyl, neopentyl or isooctyl.

Alkenyl—as a group per se and as a structural element of other groups and compounds, such as haloalkenyl—in each case taking due account of the number of carbon atoms respectively contained in the corresponding group or compound, is either straight-chain, e.g. ethenyl, propen-1-yl, but-1-en-1-yl, pent-2-en-1-yl or oct-3-en-1-yl, or branched, e.g. propen-2-yl, but-1-en-2-yl or oct-2-en-4-yl.

Alkynyl, in each case taking due account of the number of carbon atoms, is either straight-chain, e.g. ethynyl, propyn-1-yl, but-1-yn-1-yl, pent-2-yn-1-yl or oct-3-yn-1-yl, or branched, e.g. propyn-2-yl, but-1-yn-2-yl or oct-2-yn-4-yl.

Alkanoyl, in each case taking due account of the number of carbon atoms, is either straight-chain or branched, e.g. formyl, acetyl, propionyl, butyryl, pivaloyl or octanoyl.

Cycloalkyl, in each case taking due account of the number of carbon atoms, is cyclopropyl, cyclobutyl, cyclopentyl, cyclohexyl, cycloheptyl or cyclooctyl.

Cycloalkoxy, in each case taking due account of the number of carbon atoms, is cyclopropoxy, cyclobutoxy, cyclopentyloxy, cyclohexyloxy, cycloheptyloxy or cyclooctyloxy.

In halo-substituted carbon-containing groups and compounds, such as haloalkyl, haloalkenyl, haloalkoxy, haloalkylthio and haloalkanesulfonyl, at least one of the hydrogen atoms present in the underlying non-halogenated basic structure has been replaced by a halogen atom; it is possible, however, for two or more than two, for example—in the case of perhalogenation—all, of the hydrogen atoms present in the underlying non-halogenated basic structure to have been replaced, independently of one another, by halogen atoms. There may be mentioned by way of example: —CH$_2$F, —CHF$_2$, —CF$_3$, —CH$_2$Cl, —CHCl$_2$, —CCl$_3$, —CCl$_2$CCl$_3$, —CH$_2$Br, —CH$_2$CH$_2$Br, —CHBrCl, —CCl=CCl$_2$, —OCH$_2$F, —SCHCl$_2$ and —SO$_2$CF$_3$.

In alkoxy-, alkylthio-, alkanesulfinyl-, alkanesulfonyl- and cyano-substituted carbon-containing groups and compounds, such as alkoxyalkyl, alkylthioalkyl, alkanesulfinylalkyl, alkanesulfonylalkyl, cyanoalkylthio and cyanoalkanesulfonyl, one of the hydrogen atoms present in the underlying unsubstituted basic structure has been replaced by alkoxy, alkylthio, alkanesulfinyl, alkanesulfonyl or by cyano.

Preference is given within the scope of the invention to (1) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, any substituents present at the mentioned (p+5) substitutable ring carbon atoms of the two rings A and B being selected from the group consisting of halogen, C$_1$-C$_4$alkyl, halo-C$_1$-C$_4$alkyl having 1, 2 or 3 halogen atoms, C$_1$-C$_2$alkoxy-C$_1$-C$_4$alkyl, C$_3$-C$_6$cycloalkyl, C$_1$-C$_4$alkoxy, halo-C$_1$-C$_4$alkoxy having 1, 2 or 3 halogen atoms, C$_3$-C$_7$cycloalkoxy, C$_1$-C$_4$alkylthio, halo-C$_1$-C$_4$alkylthio having 1, 2 or 3 halogen atoms, cyano, nitro, phenyl, phenoxy and phenylthio, the phenyl groups in phenyl, phenoxy and phenylthio being unsubstituted or substituted by one, two or three substituents selected from the group consisting of halogen, C$_1$-C$_2$alkyl and C$_1$-C$_2$alkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

R$_1$ is hydrogen, C$_1$-C$_4$alkyl, C$_3$-C$_7$cycloalkyl, benzyl, C$_1$-C$_4$alkanoyl that is unsubstituted or substituted by halogen or by C$_1$-C$_2$alkoxy, benzoyl the phenyl group of which is unsubstituted or substituted by one or two substituents selected from the group consisting of halogen, C$_1$-C$_2$alkyl, nitro and cyano; C$_1$-C$_4$alkanesulfonyl, halo-C$_1$-C$_4$alkanesulfonyl having 1, 2 or 3 halogen atoms, cyano-$C_1$-$C_4$alkanesulfonyl or phenylsulfonyl the phenyl group of which is unsubstituted or substituted by one or two substituents selected from the group consisting of halogen, $C_1$-$C_2$alkyl, nitro and cyano;

$R_2$ and $R_3$, independently of one another, are hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl or $C_3$-$C_7$cycloalkyl;

$R_4$ is hydrogen, $C_1$-$C_4$alkyl, $C_1$-$C_4$alkoxy or $C_1$-$C_4$alkylthio;

$R_5$ is hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_2$alkylthio-$C_1$-$C_4$alkyl, $C_1$-$C_2$alkanesulfinyl-$C_1$-$C_4$alkyl, $C_1$-$C_2$alkanesulfonyl-$C_1$-$C_4$alkyl, $C_2$-$C_4$alkenyl, halo-$C_2$-$C_4$alkenyl having 1, 2 or 3 halogen atoms, $C_2$-$C_4$alkynyl, $C_3$-$C_7$cycloalkyl, $C_1$-$C_4$alkylthio or halogen;

$R_6$ is hydrogen, hydroxy, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_4$alkoxy, $C_1$-$C_4$alkylthio, $C_1$-$C_4$alkanesulfinyl, $C_1$-$C_4$alkanesulfonyl, halogen, nitro, cyano, amino, a group of the formula $N(H)R_8$(Ib), a group of the formula $N(R_8)R_9$ (Ic) or a group of the formula $N=C(R_9)R_{10}$(Id);

$R_7$ is hydrogen, $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl; $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$-$C_2$alkyl, nitro and cyano;

$R_8$ is $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl; $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$-$C_2$alkyl, nitro and cyano;

$R_9$ is $C_1$-$C_4$alkyl;

$R_{10}$ is hydrogen or $C_1$-$C_4$alkyl; and p is 1 or 2;

or, where appropriate, a tautomer thereof, in each case in free form or in the form of a salt.

(2) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$-$C_4$alkyl, halo-$C_1$-$C_4$alkyl having 1, 2 or 3 halogen atoms, $C_1$-$C_2$alkoxy-$C_1$-$C_4$alkyl, $C_3$-$C_6$cycloalkyl, $C_1$-$C_4$alkoxy, halo-$C_1$-$C_4$alkoxy having 1, 2 or 3 halogen atoms, $C_3$-$C_7$cycloalkoxy, $C_1$-$C_4$alkylthio, halo-$C_1$-$C_4$alkylthio having 1, 2 or 3 halogen atoms, cyano, nitro, phenyl, phenoxy and phenylthio, the phenyl groups in phenyl, phenoxy and phenylthio being unsubstituted or substituted by one, two or three substituents selected from the group consisting of halogen, $C_1$-$C_2$alkyl and $C_1$-$C_2$alkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

$R_1$ is hydrogen, $C_1$-$C_4$alkyl, $C_3$-$C_7$cycloalkyl, benzyl, $C_1$-$C_4$alkanoyl that is unsubstituted or substituted by halogen or by $C_1$-$C_2$alkoxy, benzoyl the phenyl group of which is unsubstituted or substituted by one or two substituents selected from the group consisting of halogen, $C_1$-$C_2$alkyl, nitro and cyano; $C_1$-$C_4$alkanesulfonyl, halo-$C_1$-$C_4$alkanesulfonyl having 1, 2 or 3 halogen atoms, cyano-$C_1$-$C_4$alkanesulfonyl or phenylsulfonyl the phenyl group of which is unsubstituted or substituted by one or two substituents selected from the group consisting of halogen, $C_1$-$C_2$alkyl, nitro and cyano;

$R_2$ and $R_3$, independently of one another, are hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl or $C_3$-$C_7$cycloalkyl;

$R_4$ is hydrogen, $C_1$-$C_4$alkyl, $C_1$-$C_4$alkoxy or $C_1$-$C_4$alkylthio;

$R_5$ is hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_2$alkylthio-$C_1$-$C_4$alkyl, $C_1$-$C_2$alkanesulfinyl-$C_1$-$C_4$alkyl, $C_1$-$C_2$alkanesulfonyl-$C_1$-$C_4$alkyl, $C_2$-$C_4$alkenyl, halo-$C_1$-$C_4$alkenyl having 1, 2 or 3 halogen atoms, $C_2$-$C_4$alkynyl, $C_3$-$C_7$cycloalkyl, $C_1$-$C_4$alkylthio or halogen;

$R_6$ is hydrogen, hydroxy, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_4$alkoxy, $C_1$-$C_4$alkylthio, $C_1$-$C_4$alkanesulfinyl, $C_1$-$C_4$alkanesulfonyl, halogen, nitro, cyano, amino, a group of the formula $N(H)R_8$(Ib), a group of the formula $N(R_8)R_9$ (Ic) or a group of the formula $N=C(R_9)R_{10}$(Id);

$R_7$ is hydrogen, $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl, $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$-$C_2$alkyl, nitro and cyano;

$R_8$ is $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl, $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$–$C_2$alkyl, nitro and cyano;
$R_9$ is $C_1$–$C_4$alkyl;
$R_{10}$ is hydrogen or $C_1$–$C_4$alkyl; and
p is 1 or 2;
or, where appropriate, a tautomer thereof, in each case in free form or in the form of a salt.

(3) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B are monosubstituted or, in the case of the saturated ring carbon atoms of the ring B, mono- or, independently of one another, di-substituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$–$C_4$alkyl and $C_1$–$C_4$alkoxy, wherein:
$R_1$ is hydrogen, $C_1$–$C_4$alkyl or $C_1$–$C_4$alkanoyl;
$R_2$ and $R_3$, independently of one another, are hydrogen or $C_1$–$C_4$alkyl;
$R_4$ is hydrogen or $C_1$–$C_4$alkyl;
$R_5$ is $C_1$–$C_4$alkyl, halo-$C_1$–$C_4$alkyl having 1, 2 or 3 halogen atoms, $C_2$–$C_4$alkynyl, $C_3$–$C_4$cycloalkyl or $C_1$–$C_4$alkylthio;
$R_6$ is $C_1$–$C_4$alkylthio, halogen, nitro or amino;
$R_7$ is hydrogen or $C_1$–$C_4$alkyl; and
p is 1 or 2;
or, where appropriate, a tautomer thereof, in each case in free form or in the form of a salt.

(4) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$–$C_4$alkyl and $C_1$–$C_4$alkoxy; wherein:
$R_1$ is hydrogen, $C_1$–$C_4$alkyl or $C_1$–$C_4$alkanoyl;
$R_2$ and $R_3$, independently of one another, are hydrogen or $C_1$–$C_4$alkyl;
$R_4$ is hydrogen;
$R_5$ is $C_1$–$C_4$alkyl;
$R_6$ is halogen;
$R_7$ is hydrogen; and
p is 1 or 2;
in free form or in the form of a salt.

(5) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, with the proviso that the group Ia is bonded in the 2-, 3-, 6- or 7-position of the bicyclic ring system of formula I formed from the two rings A and B, any substituents present at the mentioned (p+5) substitutable ring carbon atoms of the two rings A and B being selected from the group consisting of halogen, $C_1$–$C_4$alkyl and $C_1$–$C_4$alkoxy; wherein:
$R_1$ is hydrogen or $C_1$–$C_4$alkanoyl;
$R_2$ is hydrogen;
$R_3$ is $C_1$–$C_4$alkyl;
$R_4$ is hydrogen;
$R_5$ is $C_1$–$C_4$alkyl;
$R_6$ is halogen;
$R_7$ is hydrogen; and
p is 1;
in free form or in the form of a salt.

(6) Compounds of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, with the proviso that the group Ia is bonded in the 6- or 7-position of the bicyclic ring system of formula I formed from the two rings A and B, any substituents present at the mentioned (p+5) substitutable ring carbon atoms of the two rings A and B being selected from the group consisting of $C_1$–$C_2$alkyl; wherein:
$R_1$ is hydrogen or $C_1$–$C_2$alkanoyl;
$R_2$ is hydrogen;
$R_3$ is $C_1$–$C_2$alkyl;
$R_4$ is hydrogen;
$R_5$ is $C_1$–$C_2$alkyl;
$R_6$ is chlorine;
$R_7$ is hydrogen; and
p is 1;
in free form or in the form of a salt.

(7) Compounds of formula I wherein one of the (p+6) substitutable ring carbon atoms of the two rings A and B is substituted by a group Ia and the other (p+5) substitutable ring carbon atoms of the two rings A and B are unsubstituted or one of those other (p+5) substitutable ring carbon atoms of the two rings A and B, especially the ring carbon atom in the 2-position of the bicyclic ring system of formula I formed from the two rings A and B, is monosubstituted by $C_1$–$C_2$alkyl, with the proviso that the group Ia is bonded in the 7-position of the bicyclic ring system of formula I formed from the two rings A and B; wherein:
$R_1$ is hydrogen or $C_1$–$C_2$alkanoyl;
$R_2$ is hydrogen;
$R_3$ is $C_1$–$C_2$alkyl;
$R_4$ is hydrogen;

$R_5$ is $C_1$–$C_2$alkyl;
$R_6$ is chlorine;
$R_7$ is hydrogen; and
p is 1;
in free form or in the form of a salt.

Special preference is given within the scope of the invention to the compounds of formula I mentioned in Examples P-1 to P-7.22 and, where appropriate, their tautomers, in each case in free form or in the form of a salt.

Preference is given specifically within the scope of the invention to the following compounds of formula I:

(a) 2-[1-(5-chloro-6-ethyl-pyrimidin-4-ylamino)prop-1-yl]-1,2,3,4-tetrahydro-quinoline, (Example P-1);

(b) 2-[1-(5-chloro-6-ethyl-pyrimidin-4-ylamino)ethyl]-1,2,3,4-tetrahydro-quinoline (diastercoisomer 1; Example P- 1.1.1);

(c) 2-[1-( 5-chloro-5-ethyl-pyrimidin-4-ylamino )ethyl]-1,2,3,4-tetrahydro-quinoline (diastercoisomer 2; Example P- 1.1.2);

(d) 2-[1-(5-chloro-6-ethyl-pyrimidin-4-ylamino)ethyl]-6-methoxy-1,2,3,4-tetrahydro-quinoline (Example P-1.8);

(e) 6-[1-(5-chloro-6-ethyl-pyrimidin-4-ylamino)ethyl]-1,2,3,4-tetrahydro-quinoline (Example P-3.1);

(f) 7-[1-(5-chloro-6-ethyl-pyrimidin-4-ylamino)ethyl]-1,2,3,4-tetrahydro-quinoline (Example P-4.1 );

(g) a mixture of 6-[1-(5-chloro-6-ethyl-pyrimidin-4-ylamino)ethyl]-1,2,3,4-tetrahydro-quinoline and 7-[1-( 5-chloro-6-ethyl-pyrimidin-4-ylamino)ethyl]-1,2,3,4-tetrahydro-quinoline (Example P-5.1 );

(h) a mixture of 1-acetyl-6-[1-(5-chloro-6-ethyl-pyrimidin-4-ylamino)ethyl]-1,2,3,4-tetrahydro-quinoline and 1-acetyl-7-[1-(5-chloro-6-ethyl-pyrimidin-4-ylamino)ethyl]-1,2,3,4-tetrahydro-quinoline (Example P-5.5);

(i) a mixture of 1-acetyl-6-[1-(5-chloro-6-ethyl-pyrimidin-4-ylimino)prop-1-yl]-2-methyl-1,2,3,4-tetrahydro-quinoline and 1-acetyl-7-[1-(5-chloro-6-ethyl-pyrimidin-4-yl-amino)prop-1-yl]-2-methyl-1,2,3,4-tetrahydro-quinoline (Example P-5.18);

(j) a mixture of 6-[1-(5-chloro-6-ethyl-pyrimidin-4-ylamino)prop-1-yl]-2-methyl-1,2,3,4-tetrahydro-quinoline and 7-[1-(5-chloro-6-ethyl-pyrimidin-4-ylamino)prop-1-yl]-2-methyl-1,2,3,4-tetrahydro-quinoline (Example P-5.21);

(k) 1-acetyl-8-[1-(5-chloro-6-ethyl-pyrimidin-4-ylamino)ethyl]-2,3,4,5-tetrahydro-1H-benzo[b]azepine (Example P-7.7); and (l) 1-acetyl-8-[1-(5-chloro-6-ethyl-pyrimidin-4-ylamino)prop-1-yl]-2,3,4,5-tetrahydro-1H-benzo[b]azepine (Example P-7.8);

in each case in free form or in the form of a salt.

The invention relates also to a process for the preparation of the compounds of formula I and, where appropriate, the tautomers thereof, in each case in free form or in the form of a salt, which comprises, for example a) for the preparation of a compound of formula I wherein $R_7$ is hydrogen, $C_1$–$C_8$alkyl or benzyl, or where appropriate a tautomer thereof, in each case in free form or in the form of a salt, reacting a compound of the formula

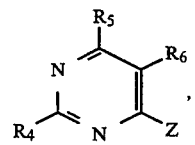
(II)

wherein $R_4$, $R_5$ and $R_6$ are as defined for formula I and Z is a readily removable nucleofugal radical or, where appropriate, a tautomer thereof with a compound of the formula

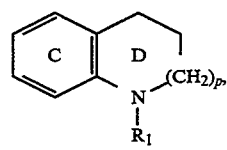
(III)

or a salt thereof, preferably in the presence of a base, and wherein $R_1$ and p are as defined for formula I and with a single exception the ring C stands for the ring A and the ring D stands for the ring B, the rings A and B being as defined for formula I, and the mentioned exception being that the place of the group Ia mentioned in formula I is taken by the group of the formula H($R_7'$)N—(C($R_2$)($R_3$)) (IIIa) wherein $R_7$ is hydrogen, $C_1$–$C_8$alkyl or benzyl and $R_2$ and $R_3$ are as defined for formula I, or b) for the preparation of a compound of formula I wherein $R_7$ is as defined for formula I but is other than hydrogen, $C_1$–$C_8$alkyl or benzyl, or, where appropriate, a tautomer thereof, in each case in free form or in the form of a salt, introducing the desired substituent $R_7$ that is other than hydrogen, $C_1$–$C_8$alkyl and benzyl into a compound of formula I wherein $R_7$ is hydrogen or, where appropriate, into a tautomer thereof, in each case in free form or in the form of a salt, by N-alkanoylation, N-benzoylation, N-alkylthiolation, N-phenylthiolation or N-benzylthiolation and in each case, if desired, converting a compound of formula I obtainable in accordance with the process or by a different method, or a tautomer thereof, in each case in free form or in the form of a salt, into a different compound of formula I or a tautomer thereof, separating a mixture of isomers obtainable in accordance with the process and isolating the desired isomer and/or converting a free compound of formula I obtainable in accordance with the process, or a tautomer thereof, into a salt or converting a salt of a compound of formula I obtainable in accordance with the process, or a tautomer thereof, into the free compound of formula I or a tautomer thereof, or into a different salt.

The statements made above regarding tautomers and salts of compounds I apply analogously also to starting materials given hereinbefore and hereinafter as regards their tautomers and salts, respectively.

The reactions described hereinbefore and hereinafter are carried out in a manner known per se, for example in the absence or, customarily, in the presence of a suitable solvent or diluent or of a mixture thereof, the reaction being carried out as required with cooling, at room temperature or with heating, for example in a temperature range of approximately from −80° C. to the boiling temperature of the reaction medium, preferably from approximately −20° C. to approximately +150° C., and, if necessary, in a closed vessel, under pressure, in an inert gas atmosphere and/or under anhydrous conditions. Especially advantageous reaction conditions are to be found in the Examples.

Variant a)

Examples of suitable radicals Z are: fluorine, chlorine, bromine, iodine, $C_1$–$C_8$alkylthio, such as methylthio, ethylthio or propylthio, $C_1$–$C_8$alkanoyloxy, such as acetoxy, (halo-)-$C_1$–$C_8$alkanesulfonyloxy, such as methanesulfonyloxy, ethanesulfonyloxy or trifluoromethanesulfonyloxy, or unsubstituted or substituted phenylsulfonyloxy, such as benzenesulfonyloxy or p-toluenesulfonyloxy, also hydroxy.

Examples of suitable bases for facilitating the removal of HZ are alkali metal or alkaline earth metal hydroxides, hydrides, amides, alkanolates, carbonates, dialkylamides or alkylsilylamides, alkylamines, alkylenediamines, unsubstituted or N-alkylated, unsaturated or saturated cycloalkylamines, basic heterocycles, ammonium hydroxides and carbocyclic amines. There may be mentioned by way of example sodium hydroxide, sodium hydride, sodium amide, sodium methanolate, sodium carbonate, potassium tert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyl-trimethylammonium hydroxide and 1,8-diazabicyclo[5.4.0]-undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halohydrocarbons, such as benzene, toluene, xylene, chlorobenzene, bromobenzene, petroleum ether, hexane, cyclohexane, dichloromethane, trichloromethane, dichloroethane or trichloroethane; ethers, such as diethyl ether, tert-butyl methyl ether, tetrahydrofuran or dioxane; ketones, such as acetone or methyl ethyl ketone; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric acid triamide; nitriles, such as acetonitrile; and sulfoxides, such as dimethyl sulfoxide. Also suitable as solvents or diluents are bases used in excess, such as triethylamine, pyridine, N-methylmorpholine or N,N-diethylaniline.

The reaction is advantageously carried out in a temperature range of from approximately 0° C. to approximately +180° C., preferably from approximately +20° C. to approximately 130° C., in many cases at the reflux temperature of the solvent used.

In a preferred form of variant a) a compound II wherein Z is halogen, preferably chlorine, is reacted with a compound III at reflux temperature, in an alcohol, preferably isopropanol, and in the presence of an alkylamine, preferably in the presence of triethylamine.

The compounds II and, where appropriate, the tautomers thereof, in each case in free form or in the form of a salt, are known or can be prepared analogously to known compounds; corresponding information is to be found, for example, on the one hand in D. J. Brown, "The Pyrimidines", in "Heterocyclic Compounds" and on the other hand in European Patent Application EP-A-0 470 600.

Some of the compounds III, in free form or in the form of a salt, are known or they can be prepared analogously to known compounds, for example as described below.

a) For example, ammonia or an amine of the formula $H_2NR_7$ (IIIb) can be reacted in customary manner in the presence of a reducing agent with a compound of formula IIIc; the compounds IIIc correspond to the compounds III, but have in place of the group IIIa that is present in compounds III a group of the formula $R_2C(=O)$—(IIId), or a group of the formula $R_3C(=O)$—(IIIe). Suitable reducing agents are, for example, hydrogen (in the presence of a hydrogenation catalyst), zinc/hydrochloric acid, sodium cyanoborohydride, sodium borohydride, iron pentacarbonyl/alcoholic potassium hydroxide or formic acid. There are thus obtained—by means of the formal replacement of the carbonyl function in groups IIId, or IIIe, by a hydrogen atom and a group of the formula $H(R_7')N$—(IIIf) compounds III having at least one hydrogen atom at the carbon atom carrying the group (IIIj).

It is also possible to use for that reaction an optionally previously prepared "combination compound" comprising the reducing agent and the compound IIIb, for example a corresponding ammonium formate or fonnamide, it being possible for the primary product having an N-formylated group IIIj that may be formed after reacting that "combined compound" with the compound IIIc then to be N-deformylated hydrolyrically in customary manner to form one of the desired compounds III.

It is also possible in customary manner to react an unsubstituted or substituted hydroxylamine with a compound IIIc, thus converting the carbonyl group into an unsubstituted or substituted oxime and reducing the latter to the corresponding amine, there being used as reducing agent, for example, complex metal hydrides, such as $LiAlH_4$, zinc/acetic acid or hydrogen (in the presence of a hydrogenation catalyst, for example in the presence of Rancy nickel or palladium on carbon). Compounds III having at least one hydrogen atom at the carbon atom carrying the group $H(R_7')N$—(IIIf) and wherein $R_7'$ is hydrogen are thus obtained.

b) It is further possible in customary manner to reduce the nitroalkyl group in nitroalkyl compounds of formula IIIs to the aminoalkyl group, the compounds IIIs corresponding to the compounds III except that they have in place of the group IIIa present in compounds III a group of the formula $O_2N$—$[C(R_2)(R_3)]$—(IIIg) and there being used as reducing agent, for example, complex metal hydrides, such as $LiAlH_4$. Compounds III wherein $R_7'$ is hydrogen are thus obtained.

c) The above-mentioned reactions a) and b) for the preparation of compounds of formula III can also be carried out using the corresponding quinoline and benzo[b]azepine derivatives, respectively, both the imino group and the nitro group, respectively, and the nitrogen-containing aromatic ring moiety being reduced, either simultaneously or in succession, to form the corresponding compounds of formula III.

d) In addition, compounds of formula III can be prepared by convening acylated 2-oxo-1,2,3,4-tetrahydroquinolines or acylated 2-oxo-2,3,4,5-tetrahydrobenz[b]azepines as described under a) and b) into the corresponding aminoalkyl-2-oxo-1,2,3,4-tetrahydro-quinolines or aminoalkyl-2-oxo-2,3,4,5-tetrahydrobenz[b]azepines, respectively, and then reducing the latter by reduction with a suitable reducing agent, such as lithium aluminium hydride or metallic sodium, to form the compounds of formula III.

Compounds III wherein $R_7'$ is hydrogen can be $C_1$–$C_8$alkylated or benzylated in customary manner to form compounds III wherein $R_7'$ is $C_1$–$C_8$alkyl or benzyl. For that purpose, for example, the compound III wherein $R_7'$ is hydrogen is reacted, advantageously in the presence of a base, for example in the presence of one of the bases indicated above, and in an inert solvent or diluent, for example of the type indicated above, with a compound of the formula $C_1$–$C_8$alkyl-Z (IIIh) or with a compound of the formula benzyl-Z (IIIi), wherein Z in each case is as defined above.

The compounds IIIb, IIIc, IIIh and IIIi are known or can be prepared analogously to known compounds.

For example, compounds of formula IIIc can be prepared by acylating corresponding non-acylated tetrahydro-quinolines or tetrahydrobenzo[b]azepines; or by acylating corresponding non-acylated quinolines or benzo[b]azepines and subsequently hydrogenating the nitrogen-containing aromatic ring moiety; if desired the carbonyl group of the acyl radical can be converted before hydrogenation into an acetal which can be hydrolysed back to the carbonyl group when hydrogenation of the nitrogen-containing aromatic ring moiety is complete.

A further possible method of preparing compounds of formula IIIc' is as follows: a compound of formula Va wherein $R_2$ and p are as defined, and wherein R is hydrogen, $C_1$–$C_8$alkyl, $C_1$–$C_4$alkoxy-$C_1$–$C_4$alkyl or $C_3$–$C_8$cycloalkyl, is first nitrated in customary manner to form a compound of formula Vb; that compound is reduced with hydrogen in the presence of a catalyst to form the aniline of formula Vc, which cyclises spontaneously to form the imine Vc', and the latter is converted using a suitable reducing agent, for example with hydrogen in the presence of a catalyst, with or without excess pressure, where appropriate in the presence of an acid, into a compound of formula IIIc wherein $R_2$, p and R are as defined.

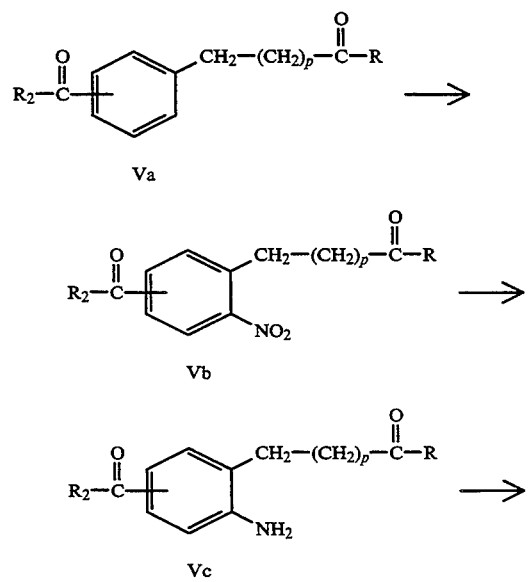

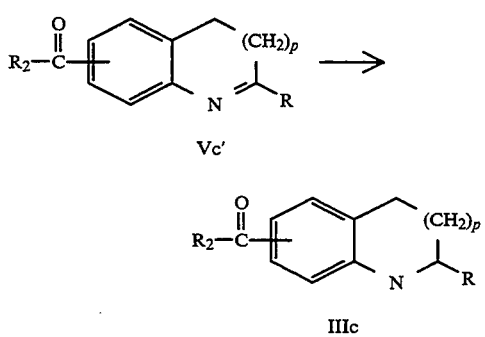

Variant b)

The N-alkanoylation, N-benzoylation, N-alkylthiolation, N-phenylthiolation or N-benzylthiolation of a compound I wherein $R_7$ is hydrogen or, where appropriate, a tautomer thereof, in each case in free form or in the form of a salt, that is obtainable, for example, in accordance with process variant a) is carried out in customary manner, for example by reacting a compound I wherein $R_7$ is hydrogen or, where appropriate, a tautomer thereof, in each case in free form or in the form of a salt, advantageously in the presence of a base, for example in the presence of one of the bases indicated under variant a), in an inert solvent or diluent, for example in an inert solvent or diluent of the type indicated under variant a), and in a temperature range of from approximately −80° C. to approximately +180° C., preferably from approximately 0° C. to approximately +130° C., in many cases at the reflux temperature of the solvent used, with a compound of the formula $C_1$–$C_8$alkanoyl-Z (Ie), with a compound of the formula phenyl-carbonyl-Z (If), the phenyl group of which is unsubstituted or substituted by one, two or three substituents selected from the group consisting of halogen and $C_1$–$C_4$alkyl, with a compound of the formula $C_1$–$C_8$alkylthio-Z (Ig), with a compound of the formula halo-$C_1$–$C_8$alkylthio-Z (Ih), with a compound of the formula cyano-$C_1$–$C_8$alkylthio-Z (Ii), with a compound of the formula phenylthio-Z (Ij) or with a compound of the formula benzylthio-Z (Ik), the phenyl groups in phenylthio and benzylthio being unsubstituted or substituted by one or two substituents selected from the group consisting of halogen, $C_1$–$C_4$alkyl, nitro and cyano.

In the compounds Ie, If, Ig, Ih, Ii, Ij and Ik, Z in each case is as defined under variant a).

The compounds Ie, If, Ig, Ih, Ii, Ij and Ik are known or can be prepared analogously to known compounds.

A compound I obtainable in accordance with the process or by a different method or, where appropriate, a tautomer thereof can be converted in a manner known per se into a different compound I by replacing one or more substituents of the starting compound I in customary manner by (an)other substituent(s) according to the invention.

For example:
non-halogen-containing substituents and non-halogenated aromatic or heteroaromatic ring part-structures can be halogenated to form halogen-containing substituents and halogenareal aromatic or heteroaromatic ring part-structures according to the invention, respectively;

halogen substituents can be exchanged for other substituents according to the invention, such as alkylthio or alkoxy substituents; in particular alkanoyl or benzoyl substituents $R_1$ can be exchanged for hydrogen $R_1$ or hydrogen $R_1$ can be exchanged for alkyl $R_1$.

The especially preferred exchange of alkanoyl or benzoyl substituents $R_1$ for hydrogen $R_1$ (deacylation) is generally effected in customary manner, but can also be carried out under special reaction conditions, for example by reacting the acylated compound I with elementary sodium in a higher secondary alcohol, such as cyclohexanol, under elevated temperature, for example in a temperature range of from 50° C. to 200° C.

In those reactions, depending on the choice of suitable reaction conditions and starting materials in each case, it is possible to replace only one substituent by another substituent according to the invention in one reaction step, or to replace several substituents by other substituents according to the invention in the same reaction step. For example, it is possible for two or more identical halogen substituents to be introduced simultaneously into the same substituent and/or ring or into various substituents and/or rings, if various substituents and/or rings are present. Likewise, for example, a substituent or ring that is already substituted, for example mono-substituted, by a specific substituent, for example chlorine, can—within the scope of the definitions of the variables according to the invention—be additionally substituted by one or more further similar substituents, for example chlorinated, i.e. can be convened, for example, into the di-substituted, for example di-chlorinated, form or into an even higher-substituted, for example higher-chlorinated, form.

Salts of compounds I can be prepared in a manner known per se. Thus, for example, acid addition salts of compounds I are obtained by treatment with a suitable acid or a suitable ion-exchange reagent, and salts with bases are obtained by treatment with a suitable base or a suitable ion-exchange reagent.

Salts of compounds I can be converted in customary manner into the free compounds I, acid addition salts, for example, by treatment with a suitable basic agent or a suitable ion-exchange reagent and salts with bases, for example, by treatment with a suitable acid or a suitable ion-exchange reagent.

Salts of compounds I can be converted in a manner known per se into other salts of compounds I; acid addition salts, for example, can be convened into other acid addition salts, for example, by treatment of a salt of an inorganic acid, such as a hydrochloride, with a suitable metal salt, such as a sodium, barium or silver salt, of an acid, for example silver acetate, in a suitable solvent in which an inorganic salt that forms, for example silver chloride, is insoluble and therefore precipitates from the reaction mixture.

Depending on the procedure and/or the reaction conditions, the compounds I having salt-forming properties are obtained in free form or in the form of salts.

The compounds I and, where appropriate, their tautomers, in each case in free form or in the form of a salt, may in some cases be present in the form of one of the possible isomers or as a mixture thereof; for example, depending on the number and absolute and relative configuration of the asymmetric carbon atoms, they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and is to be understood accordingly hereinbefore and hereinafter, even if stereochemical details are not specifically mentioned in each case.

Mixtures of diastereoisomers and mixtures of racemates of compounds I and, where appropriate, of tautomers thereof, in each case in free form or in the form of a salt, that are obtainable according to the process—depending on the starting materials and procedures chosen—or by a different method can be separated into the pure diastereoisomers or racemates in known manner on the basis of the physico-chemical differences between the constituents, for example by fractional crystallisation, distillation and/or chromatography.

Correspondingly obtainable mixtures of enantiomers, such as racemates, can be separated into the optical antipodes by known methods, for example by recrystallisation from an optically active solvent, by chromatography on chiral adsorbentg, for example high-pressure liquid chromatography (HPLC) on acetyl cellulose, with the aid of suitable microorganisms, by cleaving with specific, immobilised enzymes, by means of the formation of inclusion compounds, for example using chiral crown ethers, in which case only one enantiomer is complexed, or by conversion into diastereoisomeric salts, for example by reaction of a basic end product racemate with an optically active acid, such as a carboxylic acid, for example camphoric, tartaric or malic acid, or a sulfonic acid, for example camphorsulfonic acid, and separation of the mixture of diastereoisomers obtained in this manner, for example on the basis of their different solubilities, by fractional crystallisalion, into the diastereoisomers from which the desired enantiomer can be freed by the action of suitable, for example basic, agents.

Other than by the separation of corresponding mixtures of isomers, according to the invention pure diastereoisomers and enantiomers can be obtained by generally known methods of diastereoselective and enantioselective synthesis, respectively, for example by carrying out the process according to the invention with educts having correspondingly suitable stereochemistry.

In each case it is advantageous for the biologically more active isomer, for example enantiomer, or mixture of isomers, for example mixture of enantiomers, to be isolated or synthesised, insofar as the individual components have different biological activities.

The compounds I and, where appropriate, the tautomers thereof, in each case in free form or in the form of a salt, can also be obtained in the form of their hydrates and/or may include other solvents, for example solvents used for the crystallisation of compounds in solid form.

The invention relates to all forms of the process according to which a compound obtainable as starting material or intermediate at any stage of the process is used as starting material and all or some of the remaining steps are carried out, or a starting material is used in the form of a derivative or salt and/or its racemates or antipodes or, especially, is formed under the reaction conditions.

In the process of the present invention, it is preferable to use those starting materials and intermediates, in each case in free form or in the form of a salt, which result in the compounds I or the salts thereof described at the beginning as being especially valuable.

The invention relates especially to the preparation processes described in the Examples. The invention relates also to starting materials and intermediates, in each case in free form or in the form of a salt, used according to the invention for the preparation of the compounds I or their salts, that are novel, to their use and to processes for their preparation.

In that connection, the compounds HI are of special significance; the invention relates further to those compounds, as well as to the preparation thereof and to their use as intermediates.

Pyrimidines amino-substituted in the 4-position are already known, for example from the European Patent Application having the publication no. 0 126 254. The compounds I of the present invention differ structurally from those known compounds in a characteristic manner; in addition, the compounds I of the present invention exhibit an unexpectedly high degree of microbicidal, insecticidal and acaricidal activity.

At room temperature, the compounds I and, where appropriate, the tautomers thereof, in each case in free form or in the form of a salt, of the present invention, are stable oils, resins or solids. They can be used in the agricultural sector and related fields preventively and/or curatively as active ingredients in the control of plant-damaging microorganisms and of pests of the acaricidal type. The compounds of formula I according to the invention are distinguished—even at low rates of application—not only by outstanding activity, but also by being well tolerated by plants.

The compounds of formula I according to the invention have, for practical purposes, a very advantageous biocidal spectrum for the control of pests of the order Acarina and the class Insecta and of phytopathogenic microorganisms, especially fungi. They have very advantageous, especially systemic, properties and are used for protecting numerous cultivated plants. With the compounds of formula I it is possible to inhibit or destroy the pests which occur on plants or on parts of plants (fruit, blossoms, leaves, stems, tubers, roots) in different crops of useful plants, while at the same time the parts of plants which grow later are also protected, for example, against phytopathogenic microorganisms.

Compounds I are effective, for example, against phytopathogenic fungi belonging to the following classes: Fungi imperfecti (e.g. Botrytis, Pyricularia, Helminthosporium, Fusarium, Septoria, Cercospora and Altemaria) and Basidiomycetes (e.g. Rhizoctonia, Hemileia, Puccinia). They are also effective against the classes of the Ascomycetes (e.g. Venturia and Erysiphe, Podosphaera, Monilinia, Uncinula) and Oomycetes (e.g. Phytophthora, Pythium, Plasmopara).

The compounds I can also be used as dressing agents for protecting seeds (fruit, tubers, grains) and plant cuttings against fungal infections and against phytopathogenic fungi which occur in the soil.

The compounds I according to the invention are in addition valuable active ingredients in the control of pests of the order Acarina and the class Insecta in and on useful plants and ornamentals in agriculture, especially in plantations of cotton, vegetables and fruits, in forestry, in storage and material protection and in the hygiene sector, especially in and on domestic animals and productive livestock. They are effective against various stages of development. Their activity may manifest itself in the death of the pests immediately or only after some time, for example during shedding, or in clearly reduced oviposition and/or hatching rate. The order Acarina includes, for example, Boophilus spp. and Tetranychus spp.; the list is not limiting.

The invention relates also to the compositions that comprise compounds I as active ingredients, especially plant-protecting compositions, and to their use in the agricultural sector and related fields. The invention additionally includes the preparation of those compositions, which is characterised by the intimate mixing of the active ingredient with one or more of the compounds or groups of compounds described below. Also included in the invention is a method of treating plants, which is distinguished by the application of the novel compounds I or the novel compositions.

Target crops to be protected within the scope of the invention comprise e.g. the following species of plants: cereals (wheat, barley, rye, oats, flee, maize, sorghum and related species); beet (sugar beet and fodderbeet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor) and plants such as tobacco, nuts, coffee, aubergines, sugar cane, tea, peppers, vines, hops, bananas and natural rubber plants, as well as ornamentals.

Compounds I are normally applied in the form of compositions and can be applied to the crop area or plant to be treated, simultaneously or in succession, with further compounds. These further compounds can be, for example, fertilisers or micronutrient donors or other preparations that influence plant growth. They can also be selective herbicides, as well as insecticides, fungicides, bactericides, nematicides, molluscicicles or mixtures of several of these preparations, if desired together with further carriers, surfactants or other application-promoting adjuvants customarily employed in formulation technology.

Suitable carriers and adjuvants can be solid or liquid and are substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which comprises at least one of said compounds, is foliar application. The number of applications and the rate of application depend on the risk of infestation by the corresponding patbogen. However, the compounds I can also penetrate the plant through the roots via the soil (systemic action) if the locus of the plant is impregnated with a liquid formulation, or if the compounds are applied in solid form to the soil, e.g. in the form of granules (soil application). In paddy rice crops, such granules may be applied in metered amounts to the flooded rice field. The compounds I may, however, also be applied to seeds (coating) by impregnating the seeds either with a liquid formulation of the compound, or coating them with a solid formulation.

The compounds I are used in unmodified form or, preferably, together with the adjuvants conventionally employed in formulation technology and are for this purpose advantageously formulated in known manner e.g. into emulsifiable concentrates, coatable pastes, directly sprayable or dilutable solutions, dilute emulsions, wettable powders, soluble powders, dusts, granules and also encapsulations in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, especially from 20 g to 600 g a.i./ha.

The formulations, i.e. the compositions, preparations or mixtures comprising the compound (active ingredient) of formula I and, where appropriate, a solid or liquid adjuvant, are prepareffin known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; and water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonire; and suitable non-sorbent carriers are, for example, calcite or sand. In addition, a great number of pregranulated materials of inorganic or organic nature can be used, e.g. dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

Further surfactants customarily employed in formulation technology are known to the person skilled in the art or can be found in the relevant specialist literature.

The agrochemical compositions usually comprise 0.1 to 99 % by weight, preferably 0.1 to 95 % by weight, of a compound of formula I, 99.9 to 1% by weight, preferably 99.8 to 5 % by weight, of a solid or liquid adjuvant, and 0 to 25 % by weight, preferably 0.1 to 25 % by weight, of a surfactant.

Whereas commercial products will preferably be formulated as concentrates, the end user will normally employ dilute formulations.

The compositions may also comprise further auxiliaries such as stabilisers, antifoams, viscosity regulators, binders or tackifiers, as well as fertilisers or other active ingredients for obtaining special effects.

The Examples that follow illustrate the invention described above without limiting the scope thereof in any way. Temperatures are given in degrees Celsius. The following abbreviations are used: Ac=acetyl; Et-=ethyl; Iso-Pr=isopropyl; Me=methyl; Ph=phenyl; Pr=n-propyl; m.p.=melting point. DS=diastereoisomer; Reg=regioisomer. "NMR" represents "nuclear-magnetic resonance spectrum". MS=mass spectrum. "%" stands for "percent by weight", unless corresponding concentrations are given in a different unit. The term "compound according to the invention" is to be understood in each case as being a compound I or, where appropriate, a tautomer thereof, in each case in free form or in the form of an agrochemically acceptable salt.

PREPARATION EXAMPLES FOR COMPOUNDS OF THE INVENTION

Example P-1: 1.3 g of 2-(1-aminopropyl)-1,2,3,4-tetrahydro-quinoline, 1.4 g of 4,5-dichloro-6-ethylpyrimidine and 0.85 g of triethylamine in 60 ml of absolute isopropanol are placed in a sulfonation flask at room temperature. The internal temperature of the flask is increased to 80° C. and the reaction mixture is stirred under reflux for 12 hours. The solvent is then removed under a water-jet vacuum, the residue is taken up in a mixture of 200 ml of ethyl acetate and 70 ml of water and the mixture is shaken well. The organic phase is removed and the aqueous phase is further extracted twice, each time with 100 ml of ethyl acetate. The organic phase is dried over $Na_2SO_4$ and the solvent is removed under a water-jet vacuum. The crude product which remains can then be further purified by flash chromatography on silica gel (eluant: ethyl acetate/n-hexane 1:3) to yield 1.6 g of 2-[1-(5-chloro-6-ethylpyrimidin-4-ylamino)propyl]-1,2,3,4-tetrahydro-quinoline in the form of a red oil ($n_D^{50}$=1.5822).

Example P-2: A regioisomeric mixture of 4.5 g of 1-acetyl-6-[1-(5-chloro-6-ethyl-pyrimidin-4-ylamino)ethyl]-1,2,3,4-tetrahydro-quinoline and 1-acetyl-7-[1-(5-chloro-6-ethylpyrimidin-4-ylamino)ethyl]-1,2,3,4-tetrahydro-quinoline is dissolved at room temperature in 45 ml of approximately 4.5N ethanolic hydrochloric acid solution and then maintained under reflux for 8 hours with stirring. The solvent is then removed under a water-jet vacuum and the residue is dissolved in approximately 30 ml of water. The solution is then adjusted to pH 8 with cold 1N sodium hydroxide solution and the mixture is repeatedly extracted with diethyl ether. The combined organic phases are dried over $Na_2SO_4$ and concentrated by evaporation under a water-jet vacuum. The crude product can then be purified by flash chromatography on silica gel (eluant: ethyl acetate/n-hexane 3:1) to yield 3.2 g of a regioisomeric mixture of 6-[1-(5-chloro-6-ethylpyrimidin-4-yl-amino)ethyl]- 1,2,3,4-tetrahydro-quinoline and 7-[1-(5-chloro-6-ethylpyrimidin-4-ylamino)ethyl]-1,2,3,4-tetrahydro-quinoline (ratio approximately 1:1 from $^1$H-NMR-integration) in the form of a red oil ($^1$H-NMR).

In a manner analogous to that described in Examples P-1 and P-2, or by means of another corresponding procedure described hereinbefore, it is also possible to prepare the compounds listed in the following Tables.

TABLE 1

Compounds of formula I.1

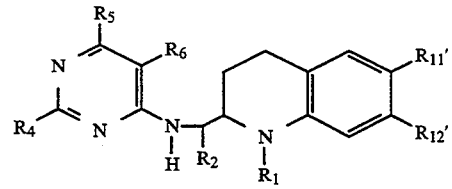

(I.1)

| Ex. P | $R_1$ | $R_2$ | $R_4$ | $R_5$ | $R_6$ | $R_{11}'$ | $R_{12}'$ | phys. data m.p. °C. |
|---|---|---|---|---|---|---|---|---|
| 1.1.1 | H | Me | H | Et | Cl | H | H | 124–125 (DS 1) |
| 1.1.2 | H | Me | H | Et | Cl | H | H | 134–136 (DS 2) |
| 1.2 | H | Me | H | Et | Br | H | H | |
| 1.3 | H | Pr | H | Me | Cl | H | H | |
| 1.4 | H | △ | H | H | Me | Cl | H | |
| 1.5 | H | Me | H | Me | Cl | H | H | |
| 1.6 | H | Et | H | Et | Br | H | H | oil |
| 1.7 | H | Et | H | Me | Cl | H | H | |
| 1.8 | H | Me | H | Et | Cl | OMe | H | 79–84 |
| 1.9 | H | Me | H | Me | Cl | OMe | H | |
| 1.10 | H | Me | H | Me | Br | OMe | H | |
| 1.11 | H | Me | H | Et | Cl | H | Cl | |
| 1.12 | H | Me | H | Et | Br | H | Cl | |
| 1.13 | H | Me | H | Me | Cl | H | Cl | |
| 1.14 | H | Et | H | Et | Cl | OMe | H | |
| 1.15 | H | Et | H | Me | Cl | OMe | H | |
| 1.16 | H | Et | H | Et | Cl | H | Cl | |
| 1.17 | H | Me | H | Et | Br | Br | H | |
| 1.18 | H | Me | H | Me | Cl | Br | H | |
| 1.19 | H | Me | H | Me | Br | Br | H | |
| 1.20 | H | Me | H | Et | NH$_2$ | H | H | |
| 1.21.1 | H | Me | H | Et | Cl | Cl | H | 148–154 (DS 1) |
| 1.21.2 | H | Me | H | Et | Cl | Cl | H | 118–120 (DS 2) |
| 1.22 | H | Et | H | Et | Cl | Cl | H | resin, $^1$H-NMR (only 1 DS) |
| 1.23 | H | Me | Me | Et | Cl | H | H | |
| 1.24.1 | H | Me | H | Et | Cl | F | H | 108–110 (DS 1) |
| 1.24.2 | H | Me | H | Et | Cl | F | H | 120–126 (DS 2) |
| 1.25 | H | Et | H | Et | Cl | F | H | |
| 1.26.1 | Ac | Me | H | Et | Cl | H | H | resin, $^1$H-NMR (DS 1) |
| 1.26.2 | Ac | Me | H | Et | Cl | H | H | 109–113 (DS 2) |
| 1.27 | H | Pr | H | Et | Cl | Me | H | oil, $n_D^{50}$ = 1.5603 |
| 1.28 | Me | Me | H | Et | Cl | H | H | |
| 1.29 | Me | Et | H | Et | Cl | H | H | |
| 1.30 | H | Me | H | Et | Cl | O—Ph | H | |
| 1.31 | H | Et | H | Et | Cl | O—Ph | H | |
| 1.32 | H | Me | H | Et | Cl | O—⟨C$_6$H$_4$⟩—F | H | |
| 1.33 | H | Et | H | Et | Cl | O—⟨C$_6$H$_4$⟩—F | H | |
| 1.34 | H | Et | H | Et | Cl | O—⟨C$_6$H$_4$⟩—Cl | H | |

TABLE 1-continued

Compounds of formula I.1

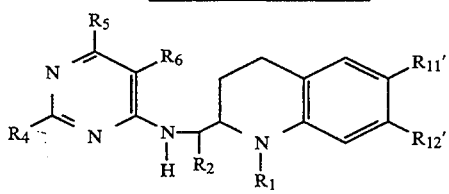

(I.1)

| Ex. P | $R_1$ | $R_2$ | $R_4$ | $R_5$ | $R_6$ | $R_{11}'$ | $R_{12}'$ | phys. data m.p. °C. |
|---|---|---|---|---|---|---|---|---|
| 1.35.1 | H | Me | H | Et | Cl | ―O―⟨=⟩―Cl (4-Cl phenoxy) | H | 82–85 (DS 1) |
| 1.35.2 | H | Me | H | Et | Cl | ―O―⟨=⟩―Cl (4-Cl phenoxy) | H | oil, $^1$H-NMR |
| 1.36 | H | Me | H | Me | Cl | ―O―⟨=⟩―Cl, Cl (2,4-diCl phenoxy) | H | |
| 1.37 | H | Me | H | Me | Cl | ―O―⟨=⟩―F, Cl (2-Cl-4-F phenoxy) | H | |
| 1.38 | H | Me | H | Et | Cl | ―O―⟨=⟩―F, Cl (2-Cl-4-F phenoxy) | H | |
| 1.39 | H | Me | Me | Et | Cl | ―O―⟨=⟩―Cl (4-Cl phenoxy) | H | |
| 1.40 | H | Me | Me | Et | Cl | ―O―⟨=⟩―F (4-F phenoxy) | H | |
| 1.41 | SO$_2$Me | Me | H | Et | Cl | H | H | |
| 1.42 | SO$_2$Ph | Me | H | Me | Cl | H | H | |
| 1.43 | H | Me | H | Et | Cl | OCF$_2$H | H | |
| 1.44 | H | Me | H | Et | Cl | OCF$_3$ | H | |
| 1.45 | H | Et | H | Et | Cl | OCF$_2$H | H | |
| 1.46 | H | Et | H | Et | Cl | OCF$_3$ | H | |

TABLE 2

Compounds of formula I.2

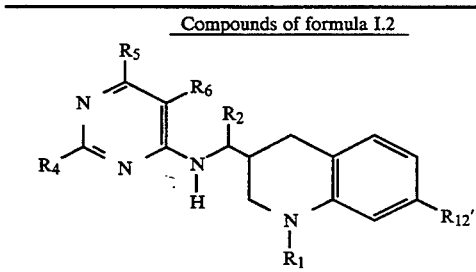

(I.2)

| Example | $R_1$ | $R_2$ | $R_4$ | $R_5$ | $R_6$ | $R_{12}'$ | phys. data |
|---|---|---|---|---|---|---|---|
| P-2.1.1 | H | Me | H | Et | Cl | H | m.p. 109–112° C. (DS 1) |
| P-2.1.2 | H | Me | H | Et | Cl | H | oil; $^1$H-NMR |
| P-2.2 | H | Me | H | Et | Br | H | |
| P-2.3 | H | Me | H | Me | Cl | H | |
| P-2.4 | H | Me | H | Et | Cl | Cl | |
| P-2.5 | H | Me | H | Et | Br | Cl | |
| P-2.6 | H | Me | H | Me | Cl | Cl | |
| P-2.7 | Ac | Me | H | Et | Cl | H | |
| P-2.8 | Me | Me | H | Et | Cl | H | |
| P-2.9 | H | Me | Me | Et | Cl | H | |
| P-2.10 | SO$_2$Me | Me | H | Et | Cl | H | |
| P-2.11 | SO$_2$Ph | Me | H | Et | Cl | H | |
| P-2.12 | H | Et | H | Et | Cl | H | |
| P-2.13 | H | △ | H | Et | Cl | H | |
| P-2.14 | Me | Et | H | Et | Cl | H | |
| P-2.15 | Me | Me | H | Et | Cl | H | |
| P-2.16 | Ac | Et | H | Et | Cl | H | |
| P-2.17 | H | Me | H | CH$_2$OMe | Cl | H | |
| P-2.18 | H | Et | H | CH$_2$OMe | Cl | H | |

TABLE 3

Compounds of formula I.3

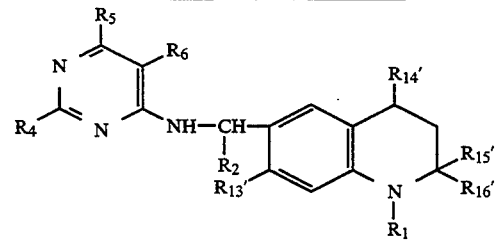

(I.3)

| Example | $R_1$ | $R_2$ | $R_4$ | $R_5$ | $R_6$ | $R_{13}'$ | $R_{14}'$ | $R_{15}'$ | $R_{16}'$ | phys. data |
|---|---|---|---|---|---|---|---|---|---|---|
| P-3.1 | H | Me | H | Et | Cl | H | H | H | H | oil; $n_D^{50}$ = 1.6002 |
| P-3.2 | H | Et | H | Et | Cl | Me | Me | Me | Me | oil, $^1$H-NMR |
| P-3.3 | H | Me | H | Et | Cl | Me | Me | Me | Me | oil; $n_D^{50}$ = 1.5658 |
| P-3.4 | Et | Me | H | Et | Cl | H | H | H | H | |
| P-3.5 | Et | Et | H | Et | Cl | H | H | H | H | |
| P-3.6 | Me | Me | H | Et | Cl | H | H | H | H | |
| P-3.7 | Me | Et | H | Et | Cl | H | H | H | H | |
| P-3.8 | Ac | Me | H | Et | Cl | H | H | H | H | |
| P-3.9 | Ac | Et | H | Et | Cl | H | H | H | H | |
| P-3.10 | H | △ | H | Et | Cl | H | H | H | H | |
| P-3.11 | H | Me | H | Et | Br | H | H | H | H | |
| P-3.12 | H | Me | H | Me | Br | H | H | H | H | |
| P-3.13 | Ac | Me | H | Et | Cl | Me | Me | Me | Me | m.p. 52–55° C. |
| P-3.14.1 | Ac | Et | H | Et | Cl | Me | Me | Me | Me | m.p. 57–60° C. (DS 1) |
| P-3.14.2 | Ac | Et | H | Et | Cl | Me | Me | Me | Me | m.p. 151–153° C. (DS 2) |
| P-3.15 | H | Me | H | Et | Cl | H | H | H | Me | |
| P-3.16 | H | Me | H | Me | Cl | H | H | H | Me | |
| P-3.17 | H | Et | H | Me | Cl | H | H | H | Me | |
| P-3.18 | H | Et | H | Et | Cl | H | H | H | Me | |
| P-3.19 | Ac | Me | H | Me | Cl | H | H | H | Me | |
| P-3.20 | Ac | Me | H | Et | Cl | H | H | H | Me | |
| P-3.21 | Ac | Et | H | Me | Cl | H | H | H | Me | |
| P-3.22 | Ac | Et | H | Et | Cl | H | H | H | Me | |
| P-3.23 | Me | Me | H | Et | Cl | H | H | H | Me | |
| P-3.24 | Me | Et | H | Et | Cl | H | H | H | Me | |
| P-3.25 | H | Et | H | Et | Cl | H | H | H | H | resin, $^1$H-NMR |
| P-3.26 | H | Et | H | Me | Cl | H | H | H | H | |

TABLE 4

Compounds of formula I.4

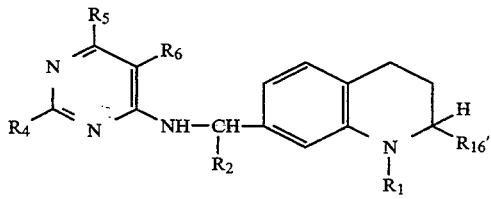
(I.4)

| Example | R$_1$ | R$_2$ | R$_4$ | R$_5$ | R$_6$ | R$_{16}'$ | phys. data |
|---|---|---|---|---|---|---|---|
| P-4.1 | H | Me | H | Et | Cl | H | oil, n$_D^{50}$ = 1.5882 |
| P-4.2 | H | Me | H | Me | Cl | H | oil |
| P-4.3 | H | Me | H | Me | Br | H | |
| P-4.4 | H | Et | H | Et | Cl | H | oil |
| P-4.5 | H | Et | H | Me | Cl | H | |
| P-4.6 | H | Et | H | Me | Br | H | |
| P-4.7 | H | Me | H | Et | Cl | Me | |
| P-4.8 | H | Me | H | Me | Cl | Me | |
| P-4.9 | H | Me | H | Me | Br | Me | |
| P-4.10 | H | Et | H | Et | Cl | Me | |
| P-4.11 | H | Et | H | Me | Cl | Me | |
| P-4.12 | H | Et | H | Me | Br | Me | |
| P-4.13 | Ac | Me | H | Et | Cl | H | m.p. 96–98° C. |
| P-4.14 | Ac | Et | H | Et | Cl | H | |
| P-4.15 | Ac | Me | H | Et | Cl | Me | |
| P-4.16 | Ac | Et | H | Et | Cl | Me | |
| P-4.17 | Ac | △ | H | Et | Cl | Me | |
| P-4.18 | CO—Et | Me | H | Et | Cl | Me | oil, $^1$H-NMR |
| P-4.19 | Me | Me | H | Et | Cl | H | |
| P-4.20 | Me | Me | H | Et | Cl | Me | oil, $^1$H-NMR |
| P-4.21 | Me | Et | H | Et | Cl | Me | |
| P-4.22 | H | Me | Me | Et | Cl | Me | |
| P-4.23 | H | Me | H | Et | Br | Me | |
| P-4.24 | Et | Me | H | Et | Cl | Me | oil, $^1$H-NMR |
| P-4.25 | H | Me | H | Et | Cl | △ | |
| P-4.26 | SO$_2$CH$_3$ | Me | H | Et | Cl | H | |
| P-4.27 | CO—Et | Me | H | Et | Cl | H | oil, $^1$H-NMR |
| P-4.28 | CO—Pr | Me | H | Et | Cl | H | |
| P-4.29 | CO—Et | Et | H | Et | Cl | H | |
| P-4.30 | CO—Pr | Et | H | Et | Cl | H | |
| P-4.31 | CO—Pr | Me | H | Et | Cl | Me | |
| P-4.32 | CO—Et | Et | H | Et | Cl | Me | |
| P-4.33 | H | Me | H | CH$_2$OCH$_3$ | Cl | H | |
| P-4.34 | H | Et | H | CH$_2$OCH$_3$ | Cl | H | |
| P-4.35 | H | Me | H | CH$_2$OCH$_3$ | Cl | Me | |
| P-4.36 | H | Et | H | CH$_2$OCH$_3$ | Cl | Me | |
| P-4.37 | Et | Et | H | Et | Cl | Me | |

TABLE 5

Mixtures of compounds of formulae (I.4) and (I.5)

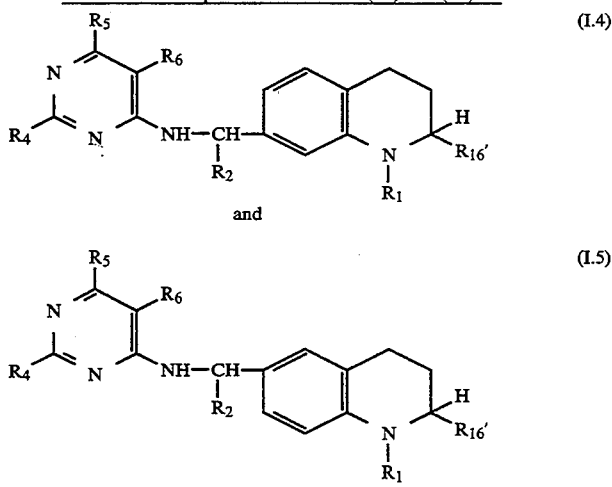

| Example | $R_1$ | $R_2$ | $R_4$ | $R_5$ | $R_6$ | $R_{16}'$ | phys. data |
|---|---|---|---|---|---|---|---|
| P-5.1 | H | Me | H | Et | Cl | H | oil |
| P-5.2 | H | Me | H | Et | Br | H | |
| P-5.3 | H | Me | H | Me | Cl | H | |
| P-5.4 | H | Me | H | Me | Br | H | |
| P-5.5 | Ac | Me | H | Et | Cl | H | oil, $^1$H-NMR |
| P-5.6 | Ac | Me | H | Et | Br | H | |
| P-5.7 | Ac | Me | H | Me | Cl | H | |
| P-5.8 | H | Et | H | Et | Cl | H | oil, $n_D^{50} = 1.5906$ |
| P-5.9 | H | Et | H | Et | Br | H | |
| P-5.10 | H | Et | H | Me | Cl | H | |
| P-5.11 | Ac | Et | H | Et | Cl | H | oil, $n_D^{50} = 1.5720$ |
| P-5.12 | Ac | Et | H | Me | Cl | H | |
| P-5.13 | H | Me | H | Et | Cl | Me | oil, $^1$H-NMR |
| P-5.14 | H | Me | H | Et | Br | Me | |
| P-5.15 | H | Me | H | Me | Cl | Me | |
| P-5.16 | H | Me | H | Me | Br | Me | |
| P-5.17 | H | Me | H | △ | Cl | Me | |
| P-5.18 | Ac | Et | H | Et | Cl | Me | oil, $n_D^{50} = 1.5634$ |
| P-5.19 | Ac | Et | H | Et | Br | Me | |
| P-5.20 | Ac | Et | H | Me | Cl | Me | |
| P-5.21 | H | Et | H | Et | Cl | Me | oil, $n_D^{50} = 1.5770$ |
| P-5.22 | H | Et | H | Me | Cl | Me | |
| P-5.23 | Me | Me | H | Et | Cl | Me | |
| P-5.24 | Me | Et | H | Et | Cl | Me | |
| P-5.25 | Me | △ | H | Et | Cl | Me | |
| P-5.26 | Me | Et | H | Me | Cl | Me | |
| P-5.27 | H | Et | H | Et | Cl | △ | |
| P-5.28 | CO—Et | Me | H | Et | Cl | Me | |
| P-5.29 | CO—Et | Et | H | Et | Cl | Me | |
| P-5.30 | CO—Et | Me | H | Et | Cl | H | |
| P-5.31 | CO—Et | Et | H | Et | Cl | H | |
| P-5.32 | CHO | Me | H | Et | Cl | H | |
| P-5.33 | CHO | Me | H | Et | Cl | Me | |
| P-5.34 | $SO_2Me$ | Me | H | Et | Cl | H | |
| P-5.35 | $SO_2Me$ | Me | H | Me | Cl | H | |
| P-5.36 | $SO_2Ph$ | Me | H | Et | Cl | H | |
| P-5.37 | H | Me | Me | Et | Cl | H | |
| P-5.38 | H | Et | Me | Et | Cl | H | |
| P-5.39 | H | Et | Me | Et | Cl | H | |
| P-5.40 | H | Me | Me | Me | Cl | Me | |
| P-5.41 | H | Et | Me | Et | Cl | Me | |
| P-5.42 | H | Me | H | $CH_2OMe$ | Cl | H | |
| P-5.43 | H | Et | H | $CH_2OMe$ | Cl | H | |
| P-5.44 | H | Me | H | $CH_2OMe$ | Cl | Me | |

TABLE 5-continued

Mixtures of compounds of formulae (I.4) and (I.5)

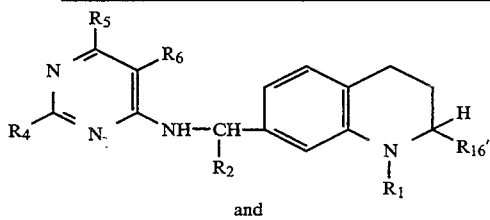

(I.4)

and

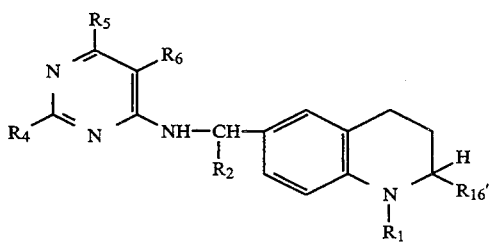

(I.5)

| Example | R₁ | R₂ | R₄ | R₅ | R₆ | R₁₆' | phys. data |
|---|---|---|---|---|---|---|---|
| P-5.45 | H | Et | H | CH₂OMe | Cl | Me | |
| P-5.46 | Me | Me | H | CH₂OMe | Cl | Me | |
| P-5.47 | Me | Et | H | CH₂OMe | Cl | Me | |

TABLE 6

Compounds of formula I.6

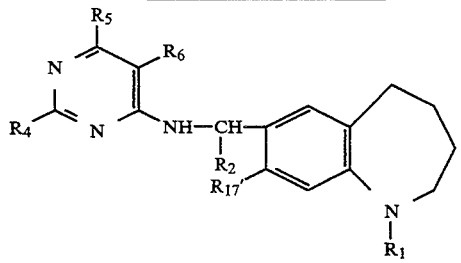

(I.6)

| Example | R₁ | R₂ | R₄ | R₅ | R₆ | R₁₇' | phys. data |
|---|---|---|---|---|---|---|---|
| P-6.1 | H | Me | H | Et | Cl | H | oil, $n_D^{50}$ = 1.5810 |
| P-6.2 | H | Me | H | Et | Br | H | |
| P-6.3 | H | Me | H | Me | Cl | H | |
| P-6.4 | H | Me | H | CF₃ | Cl | H | |
| P-6.5 | H | Me | H | SCH₃ | Cl | H | |
| P-6.6 | Ac | Me | H | Et | Cl | H | m.p. 52–55° C. |
| P-6.7 | Ac | Me | H | Et | Br | H | |
| P-6.8 | Ac | Me | H | Me | Cl | H | |
| P-6.9 | H | Et | H | Et | Cl | H | oil |
| P-6.10 | H | Et | H | Et | Br | H | |
| P-6.11 | H | Et | H | Me | Cl | H | |
| P-6.12 | H | Et | H | Me | Br | H | |
| P-6.13 | Ac | Et | H | Et | Cl | H | oil |
| P-6.14 | Ac | Et | H | Et | Br | H | |
| P-6.15 | Ac | Et | H | Me | Cl | H | |
| P-6.16 | H | Me | H | Et | Cl | OMe | |
| P-6.17 | H | Me | H | Me | Cl | OMe | |
| P-6.18 | Me | Me | H | Et | Cl | H | |
| P-6.19 | Me | Et | H | Et | Cl | H | |
| P-6.20 | CO—Et | Me | H | Et | Cl | H | |
| P-6.21 | CHO | Me | H | Et | Cl | H | |
| P-6.22 | H | △ | H | Me | Cl | H | |
| P-6.23 | H | Me | Me | Et | Cl | H | |
| P-6.24 | SO₂Me | Me | H | Et | Cl | H | |

TABLE 7

Compounds of formula I.7

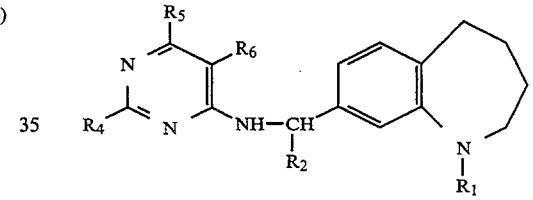

(I.7)

| Example | R₁ | R₂ | R₄ | R₅ | R₆ | phys. data |
|---|---|---|---|---|---|---|
| P-7.1 | H | Me | H | Et | Cl | oil |
| P-7.2 | H | Me | H | Me | Cl | |
| P-7.3 | H | Me | H | Me | Br | |
| P-7.4 | H | Et | H | Et | Cl | oil, $n_D^{50}$ = 1.5770 |
| P-7.5 | H | Et | H | Me | Cl | |
| P-7.6 | H | Et | H | Me | Br | |
| P-7.7 | Ac | | H | Et | Cl | resin, ¹H-NMR |
| P-7.8 | Ac | | H | Et | Cl | oil, $n_D^{50}$ = 1.5610 |
| P-7.9 | CO—Et | | H | Et | Cl | |
| P-7.10 | CO—Et | | H | Et | Cl | |
| P-7.11 | H | | H | Et | Cl | |
| P-7.12 | Ac | | H | Et | Cl | |
| P-7.13 | Me | | H | Et | Cl | |
| P-7.14 | Me | | H | Et | Cl | |
| P-7.15 | Me | | H | Me | Cl | |
| P-7.16 | | Me | H | Et | Cl | |
| P-7.17 | H | Me | Me | | Br | |
| P-7.18 | CHO | | H | Et | Cl | |
| P-7.19 | CHO | | H | Et | Cl | |
| P-7.20 | SO₂Me | | H | Et | Cl | |
| P-7.21 | SO₂Me | | H | Me | Cl | |
| P-7.22 | SO₂Ph | | H | Et | Cl | |

Preparation Examples for Intermediates

Example P-8: 2.25 g of 2-acetylquinoline are dissolved in 110 ml of absolute CH₃OH in a hydrogenation autoclave. After the addition of 0.5 g of Raney nickel and 4 g of dry ammonia the temperature is increased to 100° and the mixture is hydrogenated for 30 hours under a pressure of 2.5×10⁶ to 2.7×10⁶ Pa. Subsequently, a further 0.5 g of Raney nickel is added and the mixture is hydrogenated for a further 10 hours. After cooling, the catalyst is filtered off and the solvent is evaporated off under a water-jet vacuum. The residue is purified by means of flash chromatography on a short silica gel column [eluant: first ethanol/diethyl ether (1:1), then ethanol] to yield 2-[(1-aminoethyl)-1,2,3,4-tetrahydro]-quinoline in the form of a light-brown oil which, according to $^1$H-NMR, is in the form of a diastereoisomeric mixture (1.35:1).

Example P-9:10.7 g of a mixture consisting of t-acetyl-2-methyl-6-propionyl-1,2,3,4-tetrahydro-quinoline and 1-acetyl-2-methyl-7-propionyl-1,2,3,4-tetrahydro-quinoline, and 7.9 g of $NH_3$ (anhydrous), 0.05 g of glacial acetic acid and 2.0 g of Raney nickel in 120 ml of absolute ethanol are placed in a hydrogenation autoclave. The internal temperature is then increased to 100° and the mixture is hydrogenated for 7 hours. A further 2.0 g of Raney nickel are subsequently added and the mixture is hydrogenated for a further 12 hours. When the absorption of hydrogen has ceased, the catalyst is filtered off. After the solvent, including the excess ammonia, has been evaporated off under a water-jet vacuum, a residue remains which is purified by flash chromatography on silica gel (eluant: first diethyl ether, then ethanol) to yield a mixture of 1-acetyl-6-[(1-aminoprop-1-yl)-2-methyl-1,2,3,4-tetrahydro]quinoline and 1-acetyl-7-[(1-aminoprop-1-yl)-2-methyl-1,2,3,4-tetrahydro]-quinoline in the form of a red oil ($n_D^{50}$=1.5365).

Example P-10:0.6 g of lithium aluminium hydride in 30 ml of absolute dioxane are placed under nitrogen in a sulfonation flask. The internal temperature is then increased to approximately 70° C. and a solution of 1.2 g of 6-(1-aminopropyl)-3,4-dihydro-quinolin-2-one in 30 ml of absolute dioxane is added dropwise over a period of 10 minutes. The batch is then stirred for 6 hours at an internal temperature of approximately 80°-85° C. and allowed to cool, and, while cooling with ice, water is added dropwise until all the excess lithium aluminium hydride has reacted. Approximately 40 ml of dioxane and sodium sulfate (approximately 10 g) are then added. After having stood for a short while, the batch is suction-filtered and the dioxane is removed under a water-jet pump vacuum. The dark-brown oil which remains can then be further purified by flash chromatography on silica gel (eluant: ethanol/ether 1:1) to yield 1.0 g of 6-(1-aminopropyl)-1,2,3,4-tetrahydro-quinoline in the form of a brown oil ($^1$H-NMR).

Example P-11: 4.0 g of 2-propionylquinoline-oxime and 2 g of 5 % Pd/C catalyst in 40 ml of glacial acetic acid are placed in a hydrogenation apparatus. The batch is hydrogenated for 5 hours at 20°-25° C. under normal pressure. Filtration is then carried out, the glacial acetic acid is removed under a water-jet vacuum and the residue is purified by means of flash chromatography on silica gel (eluant: ethanol/ether 1:1 ) to yield 3.6 g of 2-(1-aminopropyl)quinoline in the form of a red oil ($^1$H-NMR).

Example P-12:9.2 g of 6-propionyl-3,4-dihydro-quinolin-2-one-oxime, 10 g of dry ammonia and 3 g of Raney nickel in 130 ml of absolute methanol are placed in a hydrogenation autoclave. The batch is hydrogenated for 12 hours at a temperature of 50° C. and a pressure of 70 bar. The catalyst is then filtered off and the solvent, as well as the excess $NH_3$, is removed under a water-jet vacuum. Purification is carried out by flash chromatography (eluant: ethanol/ether 1:3), yielding 8.2 g of 6-(1-aminopropyl)-3,4-dihydro-quinolin-2-one.

Example P-13:1.3 g of 7-(1-aminoethyl)-1,2,3,4-tetrahydro-quinoline, 0.73 g of dimethyl sulfate and 0.27 g of ground magnesium oxide in 50 ml of absolute toluene are placed in a sulfonation flask. The internal temperature is then increased to 100°-105° C. and the mixture is stirred at that temperature for 18 hours. After cooling, inorganic material is filtered off, 10 ml of conc. HCl are added to the toluene solution, and the batch is maintained at 70° C. for 2 hours. The batch is then neutralised with sodium hydroxide solution and the organic phase is removed. The aqueous phase is subsequently further extracted twice with ethyl acetate and the organic phases are dried over $Na_2SO_4$. After removal of the solvent under a water-jet vacuum, 1.2 g of crude product are obtained which can be purified by flash chromatography on silica gel (eluant: ethyl acetate/n-hexane 1: 1) to yield 1.05 g of 7-(1-aminoethyl)-1-methyl-1,2,3,4-tetrahydro-quinoline in the form of a red oil ($^1$H-NMR).

In a manner analogous to that described in Examples P-8 to P-12, or by means of another corresponding procedure described hereinbefore, it is also possible to prepare the compounds listed in the following Tables.

TABLE 8

Compounds of formula III.8

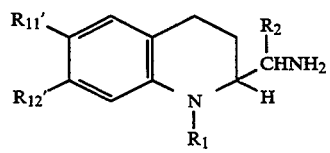

(III.8)

| Example | $R_1$ | $R_2$ | $R_{11}'$ | $R_{12}'$ | phys. data |
|---|---|---|---|---|---|
| P-8.1 | H | Et | H | H | oil, $^1$H-NMR |
| P-8.2 | H | Me | OMe | H | oil, $n_D^{50}$ = 1.5410 |
| P-8.3 | H | Bu | H | H | |
| P-8.4 | H | Et | OMe | H | |
| P-8.5 | H | Et | H | H | |
| P-8.6 | H | Pr | OMe | H | oil, $^1$H-NMR |
| P-8.7 | H | Me | F | H | oil, $n_D^{50}$ = 1.5458 |
| P-8.8 | H | Et | F | H | |
| P-8.9 | H | Me | Cl | H | oil, $^1$H-NMR |
| P-8.10 | H | Et | Cl | H | oil, $^1$H-NMR |
| P-8.11 | H |  | H | H | |
| P-8.12 | H |  | Cl | H | |
| P-8.13 | Me | Me | H | H | |
| P-8.14 | Et | Me | H | H | |
| P-8.15 | H | Me | H | Cl | |
| P-8.16 | H | Et | H | Cl | |
| P-8.17 | H | Pr | H | H | |
| P-8.18 | H | Me | OEt | H | oil |
| P-8.19 | H | Me | $OCF_3$ | H | |
| P-8.20 | H | Et | $OCF_3$ | H | |
| P-8.21 | H | Me | $OCHF_2$ | H | |
| P-8.22 | H | Et | $OCHF_2$ | H | |
| P-8.23 | H | Me | OPh | H | |
| P-8.24 | H | Et | OPh | H | |
| P-8.25 | H | Me | 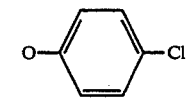 | H | oil, MS ($M^+$ = 303) |

TABLE 8-continued

Compounds of formula III.8 (III.8)

| Example | $R_1$ | $R_2$ | $R_{11}'$ | $R_{12}'$ | phys. data |
|---|---|---|---|---|---|
| P-8.26 | H | Et | -O-C6H4-Cl (4-Cl) | H | oil, $^1$H-NMR |
| P-8.27 | H | Me | -O-C6H4-F (4-F) | H | |
| P-8.28 | H | Et | -O-C6H4-F (4-F) | H | |
| P-8.29 | H | Me | -O-C6H3-Cl2 (2,4-diCl) | H | |
| P-8.30 | H | Et | -O-C6H3-Cl2 (2,4-diCl) | H | |
| P-8.31 | H | Me | -O-C6H3-ClF (2-Cl,4-F) | H | |
| P-8.32 | H | Et | -O-C6H3-ClF (2-Cl,4-F) | H | |
| P-8.33 | SO2Me | Me | H | H | |
| P-8.34 | SO2Ph | Me | H | H | |

TABLE 9

Compounds of formula III.9 (III.9)

| Example | $R_1$ | $R_2$ | $R_{12}'$ | phys. data |
|---|---|---|---|---|
| P-9.1 | H | Me | H | oil, $^1$H-NMR |
| P-9.2 | H | Me | Cl | |
| P-9.3 | H | Et | H | |
| P-9.4 | H | cyclopropyl | H | |
| P-9.5 | Me | Me | H | |
| P-9.6 | Me | Et | H | |
| P-9.7 | Et | Me | H | |
| P-9.8 | Ac | Me | H | |
| P-9.9 | Ac | Et | H | |

TABLE 10

Compounds of formula III.10 (III.10)

| Example | $R_1$ | $R_2$ | $R_{13}'$ | $R_{14}'$ | $R_{15}'$ | $R_{16}'$ | phys. data |
|---|---|---|---|---|---|---|---|
| P-10.1 | H | Me | H | H | H | H | oil, $^1$H-NMR |
| P-10.2 | H | Et | Me | Me | Me | Me | oil, $n_D^{50}$ = 1.5404 |
| P-10.3 | H | Me | Me | Me | Me | Me | oil |
| P-10.4 | Et | Me | H | H | H | H | |
| P-10.5 | Et | Et | H | H | H | H | |
| P-10.6 | H | Me | H | H | H | Me | |
| P-10.7 | H | Et | H | H | H | Me | |
| P-10.8 | Ac | Me | Me | Me | Me | Me | oil, $n_D^{50}$ = 1.5295 |
| P-10.9 | Ac | Et | Me | Me | Me | Me | m.p. 76–80° C. |
| P-10.10 | H | cyclopropyl | H | H | H | H | |
| P-10.11 | Ac | Me | H | H | H | Me | |
| P-10.12 | Ac | Et | H | H | H | Me | |
| P-10.13 | Me | Me | H | H | H | H | |
| P-10.14 | Me | Et | H | H | H | H | |
| P-10.15 | Me | Me | H | H | H | Me | |
| P-10.16 | Me | Et | H | H | H | Me | |
| P-10.17 | H | cyclopropyl | H | H | H | Me | |

TABLE 11

Compounds of formula III.11 (III.11)

| Example | $R_1$ | $R_2$ | $R_{16}'$ | phys. data |
|---|---|---|---|---|
| P-11.1 | H | Me | H | oil, $^1$H-NMR |
| P-11.2 | H | Et | H | oil |
| P-11.3 | H | Me | Me | |
| P-11.4 | H | Et | Me | |

TABLE 11-continued

Compounds of formula III.11

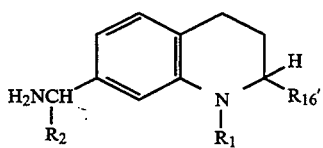
(III.11)

| Example | R₁ | R₂ | R₁₆' | phys. data |
|---|---|---|---|---|
| P-11.5 | Ac | Me | H | |
| P-11.6 | Ac | Et | H | |
| P-11.7 | Me | Et | H | |
| P-11.8 | H | △ | H | |
| P-11.9 | H | △ | Me | |
| P-11.10 | Et | Me | H | |
| P-11.11 | Me | Me | Me | |
| P-11.12 | Me | Et | Me | |

TABLE 12

Mixtures of compounds of formulae III.11 and III.12

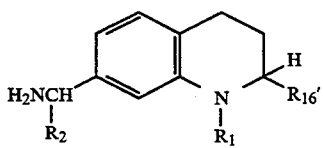
(III.11)

and

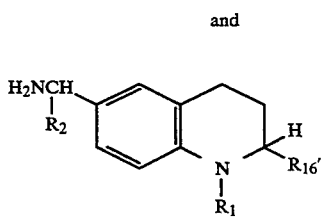
(III.12)

| Example | R₁ | R₂ | R₁₆' | phys. data |
|---|---|---|---|---|
| P-12.1 | H | Me | H | |
| P-12.2 | Ac | Me | H | oil, $n_D^{50} = 1.5342$ |
| P-12.3 | H | Et | H | oil |
| P-12.4 | Ac | Et | H | oil, $n_D^{50} = 1.5720$ |
| P-12.5 | H | Me | Me | |
| P-12.6 | H | Et | Me | |
| P-12.7 | CO—Et | Et | Me | oil |
| P-12.8 | H | △ | H | |
| P-12.9 | Me | Me | H | |
| P-12.10 | Me | Et | H | |
| P-12.11 | Me | Me | Me | |
| P-12.12 | Me | Et | Me | |

TABLE 13

Compounds of formula III.13

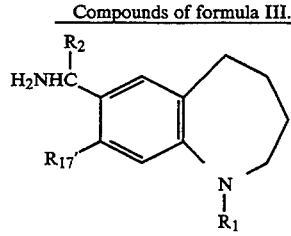
(III.13)

| Example | R₁ | R₂ | R₁₇' | phys. data |
|---|---|---|---|---|
| P-13.1 | H | Me | H | oil, ¹H-NMR |
| P-13.2 | Ac | Me | H | oil, ¹H-NMR |
| P-13.3 | H | Et | H | |
| P-13.4 | Ac | Et | H | |
| P-13.5 | H | Me | OMe | |
| P-13.6 | Me | Me | H | |
| P-13.7 | Me | Et | H | |
| P-13.8 | H | △ | H | |
| P-13.9 | Me | △ | H | |
| P-13.10 | H | △ | OMe | |
| P-13.11 | CO—Et | Me | H | |
| P-13.12 | CO—Et | Et | H | |
| P-13.13 | CHO | Me | H | |
| P-13.14 | Et | Et | H | |
| P-13.15 | Et | Me | H | |

TABLE 14

Compounds of formula III.14

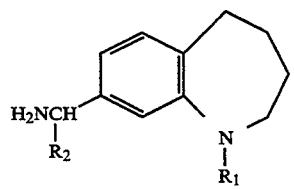
(III.14)

| Example | R₁ | R₂ | phys. data |
|---|---|---|---|
| P-14.1 | H | Me | oil |
| P-14.2 | H | Et | oil, ¹H-NMR |
| P-14.3 | Ac | Me | oil, $n_D^{50} = 1.5443$ |
| P-14.4 | Ac | Et | oil, $n_D^{50} = 1.5418$ |
| P-14.5 | CO—Et | Me | |
| P-14.6 | CO—Et | Et | |
| P-14.7 | H | △ | |
| P-14.8 | Ac | △ | |
| P-14.9 | Me | Me | |
| P-14.10 | Et | Me | |
| P-14.11 | Me | Et | |
| P-14.12 | Et | Et | |

TABLE 15

Compounds of formula III.15

(III.15) — quinoline with $R_{11}'$ at 6-position, $R_{12}'$ at 7-position, and $CHR_2NH_2$ at 2-position

| Example | $R_2$ | $R_{11}'$ | $R_{12}'$ | phys. data |
|---|---|---|---|---|
| P-15.1 | Me | H | H | oil, $n_D^{50} = 1.6084$ |
| P-15.2 | Pr | H | H | |
| P-15.3 | cyclopropyl | H | H | |
| P-15.4 | Me | Cl | H | oil, $^1$H-NMR |
| P-15.5 | Et | Cl | H | oil, MS (M$^+$ = 221) |
| P-15.6 | cyclopropyl | Cl | H | |
| P-15.7 | Me | F | H | m.p. 100–104° C. |
| P-15.8 | Et | F | H | |
| P-15.9 | Me | OMe | H | m.p. 64–65° C. |
| P-15.10 | Et | OMe | H | |
| P-15.11 | Me | OCF$_3$ | H | |
| P-15.12 | Et | OCF$_3$ | H | |
| P-15.13 | Me | OCHF$_2$ | H | |
| P-15.14 | Et | OCHF$_2$ | H | |
| P-15.15 | Me | O—Et | H | m.p. 115–118° C. |
| P-15.16 | Et | O—Et | H | |
| P-15.17 | Pr | OMe | H | oil, $n_D^{50} = 1.5590$ |
| P-15.18 | Me | OPh | H | |
| P-15.19 | Et | OPh | H | |
| P-15.20 | Me | O-(4-Cl-C$_6$H$_4$) | H | oil, $^1$H-NMR |
| P-15.21 | Et | O-(4-Cl-C$_6$H$_4$) | H | oil, $^1$H-NMR |
| P-15.22 | Me | O-(4-F-C$_6$H$_4$) | H | |
| P-15.23 | Et | O-(4-F-C$_6$H$_4$) | H | |
| P-15.24 | Me | O-(2,4-Cl$_2$-C$_6$H$_3$) | H | |
| P-15.25 | Et | O-(2,4-Cl$_2$-C$_6$H$_3$) | H | |
| P-15.26 | Me | O-(2-Cl-4-F-C$_6$H$_3$) | H | |
| P-15.27 | Et | O-(2-Cl-4-F-C$_6$H$_3$) | H | |
| P-15.28 | Me | H | Cl | |
| P-15.29 | Et | H | Cl | |

TABLE 16

Compounds of formula III.16

(III.16) — quinoline with $R_{12}'$ at 7-position and $CHNH_2R_2$ at 3-position

| Example | $R_2$ | $R_{12}'$ | phys. data |
|---|---|---|---|
| P-16.1 | Me | H | oil, $^1$H-NMR |
| P-16.2 | Et | H | |
| P-16.3 | cyclopropyl | H | |
| P-16.4 | Me | Cl | |
| P-16.5 | Et | Cl | |

TABLE 17

Compounds of formula III.17

(III.17) — quinoline with $H_2NCHR_2$ at 6-position and $R_{16}'$ at 2-position

| Example | $R_2$ | $R_{16}'$ | phys. data |
|---|---|---|---|
| P-17.1 | Me | H | oil, $^1$H-NMR |
| P-17.2 | Et | H | |
| P-17.3 | cyclopropyl | H | |
| P-17.4 | Me | Me | |
| P-17.5 | Et | Me | |
| P-17.6 | cyclopropyl | Me | |
| P-17.7 | Pr | Me | |

TABLE 18

Compounds of formula III.18

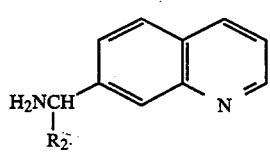
(III.18)

| Example | R₂ | phys. data |
|---|---|---|
| P-18.1 | Me | oil, ¹H-NMR |
| P-18.2 | Et | oil |
| P-18.3 | Pr | |
| P-18.4 | △ | |
| P-18.5 | cyclopentyl | |

TABLE 19

Compounds of formula III.19

(III.19)

| Example | R₁ | R₂ | phys. data |
|---|---|---|---|
| P-19.1 | H | Me | m.p. 147–150° C. |
| P-19.2 | H | Pr | |
| P-19.3 | H | △ | |
| P-19.4 | Me | Me | |
| P-19.5 | Me | Et | |
| P-19.6 | Me | △ | |

TABLE 20

Compounds of formula III.20

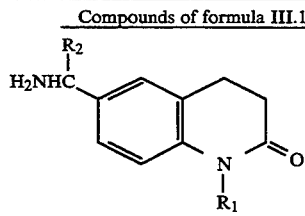
(III.20)

| Example | R₁ | R₂ | phys. data |
|---|---|---|---|
| P-20.1 | H | Me | |
| P-20.2 | H | Et | |
| P-20.3 | H | △ | |
| P-20.4 | Me | Me | |
| P-20.5 | Me | Et | |
| P-20.6 | Me | △ | |
| P-20.7 | Et | Me | |
| P-20.8 | Et | Et | |

TABLE 21

Compounds of formula III.21

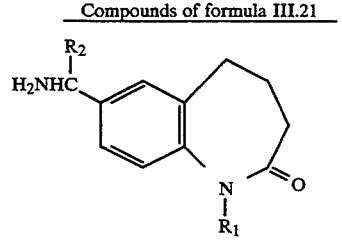
(III.21)

| Example | R₁ | R₂ | phys. data |
|---|---|---|---|
| P-21.1 | H | Me | wax, ¹H-NMR |
| P-21.2 | H | Et | oil, ¹H-NMR |
| P-21.3 | H | △ | |
| P-21.4 | Me | Me | |
| P-21.5 | Me | Et | |
| P-21.6 | Me | △ | |
| P-21.7 | Et | Me | |
| P-21.8 | Et | Et | |

TABLE 22

Compounds of formula III.22

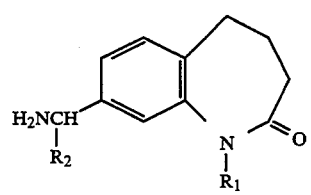
(III.22)

| Example | R₁ | R₂ | phys. data |
|---|---|---|---|
| P-22.1 | H | Me | |
| P-22.2 | H | Et | oil, ¹H-NMR |
| P-22.3 | H | △ | |
| P-22.4 | Me | Me | |
| P-22.5 | Me | Et | |
| P-22.6 | Me | △ | |

The following Table 23 contains the ¹H-NMR data of the afore-mentioned compounds. The recording of the ¹H-NMR spectra was carded out in CDCl₃ if no other solvent is specified. DS is an abbreviation for diastereoisomer and Reg is an abbreviation for regioisomer.

TABLE 23

| Example | $^1$H-NMR data (ppm/multiplicity/number of protons) |
|---|---|
| P-2 | 1.28/2xt/6H (Reg 1 and Reg 2); 1.57/d/6H (Reg 1 and Reg 2); 1.95/m/2H (Reg 1 and Reg 2); 2.68–2.82/m/6H (Reg 1 and Reg 2); 3.30/m/4H (Reg 1 and Reg 2); 5.23/m/2H (Reg 1 and Reg 2); 5.45–5.65/2xd/2H (Reg 1 and Reg 2); 6.49–7.02/m/6H (Reg 1 and Reg 2); 8.41/s/1H (Reg 1 or Reg 2); 8.42/s/1H (Reg 1 or Reg 2) |
| P-1.22 | 1.02/t/3H; 1.28/t/3H; 1.52–1.60/m/2H; 1.78/m/1H; 1.95/m/1H; 2.80/q/2H; 3.51/m/1H; 4.40/m/1H; 4.52/s/1H; 5.15/d/1H; 6.29/d/1H; 6.86/dd/1H; 6.89/d/1H; 8.42/s/1H |
| P-1.26.1 | 1.28/d+t/6H; 1.45/m/1H; 2.07/s/3H; 2.50/m/2H; 2.75/m/1H; 2.80/q/2H; 3.89/m/1H; 4.98/q/1H; 6.65/d/1H; 6.87/d/1H; 7.11–7.21/m/3H; 8.39/s/1H |
| P-1.35.2 | 1.38/d/3H; 1.62/m/1H; 2.01/m/1H; 2.80–2.90/m/4H; 3.42/m/1H; 4.39/m/1H; 6.58/d/1H; 6.69/m/2H; 6.88/d/1H; 7.18–7.30/m/4H; 8.43/s/1H |
| P-2.12 | 1.29/t/3H; 1.32/d/3H; 2.18/m/1H; 2.68/m/1H; 2.79/q/2H; 2.90/dd/1H; 3.15/m/1H; 3.41/m/1H; 4.48/m/1H; 6.51/d/1H; 6.65/tr/1H; 6.98/m/2H; 8.40/s/1H |
| P-3.25 | 0.90/t/3H; 1.22/t/3H; 1.79–2.02/m/4H; 2.75/m/4H; 3.29/t/2H; 3.82/s/1H; 5.0/q/1H; 5.53/d/1H; 6.45/d/1H; 6.93/m/2H; 8.40/s/1H |
| P-4.18 | 1.12/t/3H; 1.25/t/3H; 1.60/o/3H; 1.94/m/2H; 2.43/q/2H; 2.70/t/2H; 2.78/q/2H; 3.75/m/1H; 5.30/q/1H; 5.59/d/1H; 7.07–7.14/m/2H; 7.27/s/1H; 8.37/s/1H |
| P-4.20 | 1.24/t/3H; 1.58/d/3H; 1.96/m/2H; 2.78/m/4H; 2.90/s/3H; 3.22/t/2H; 5.26/m/1H; 5.59/d/1H, 6.57/s/1H; 6.61/dd/1H; 6.93/o/1H; 8.41/s/1H |
| P-4.24 | 1.11/t/3H; 1.24/t/3H; 1.58/d/3H; 1.94/m/2H; 2.70–2.81/m/4H; 3.24/t/2H; 3.33/q/2H; 5.24/m/1H; 5.59/d/1H; 6.54–6.59/m/2H; 6.92/d/1H; 8.41/s/1H |
| P-4.27 | 1.12/t/3H; 1.25/t/3H; 1.60/d/3H; 1.94/m/2H; 2.43/q/2H; 2.70/t/2H; 2.78/q/2H; 3.75/m/1H; 5.30/q/1; 5.59/d/1H; 7.07–7.14/m/2H; 7.27/s/1H; 8.37/s/1H |
| P-5.5 | 1.20–1.35/m/6H (Reg 1 and Reg 2); 1.56–1.65/2xd/6H (Reg 1 and Reg 2); 1.88–2.02/m/4H (Reg 1 and Reg 2); 2.18/s/3H (Reg 1 or Reg 2); 2.25/s/3H (Reg 1 or Reg 2). 2.65–2.85/m/8H (Reg 1 and Reg 2); 3.80/t/4H (Reg 1 and Reg 2); 5.32/m/2H (Reg 1 and Reg 2); 5.59/t/2H (Reg 1 and Reg 2); 7.05–7.25/m/6H (Reg 1 and Reg 2); 8.38/s/1H (Reg 1 and Reg 2); 8.41/s/1H (Reg 1 or Reg 2) |
| P-8 | 1.12/d/3H (DS 1 or DS 2); 1.18/d/3H (DS 1 or DS 2); 1.60–2.08/m/8H (DS 1 and DS 2); 2.69–2.88/m/5H (DS 1 and DS 2); 2.95/m/1H (DS 1 or DS 2); 3.08/m/1H (DS 1 or DS 2); 3.18/m/1H (DS 1 or DS 2); 6.49–6.61/m/4H (DS 1 and DS 2); 6.95/m/4H (DS 1 and DS 2) |
| P-8.1 | 1.05/2xt/6H (DS 1 and DS 2); 1.20–2.05/m/8H (DS 1 and DS 2); 2.51/m/1H (DS 1 or DS 2); 2.70–2.90/m/2H (DS 1 and DS 2); 3.05/m/1H (DS 1 or DS 2); 3.25/m/2H (DS 1 and DS 2); 6.48–6.68/m/4H (DS 1 and DS 2); 6.90–7.0/m/4H (DS 1 and DS 2) |
| P-8.6 | 0.99/2xt/6H (DS 1 and DS 2); 1.15–2.05/m/12H (DS 1 and DS 2); 2.55–2.90/m/6H (DS 1 and DS 2); 2.98/m/1H (DS 1 or DS 2); 3.15/m/1H (DS 1 or DS 2); 6.48–6.62/m/6H (DS 1 and DS 2) |
| P-8.9 | 1.10/d/3H (DS 1 or DS 2); 1.18/d/3H (DS 1 or DS 2); 1.50–2.05/m/4H (DS 1 and DS 2); 2.65–2.93/m/5H (DS 1 and DS 2); 3.05–3.20/m/3H (DS 1 and DS 2); 6.45/m/2H (DS 1 and DS 2); 6.92/m/4H (DS 1 and DS 2) |
| P-9.1 | 1.10–1.20/2xd/6H (DS 1 and DS 2); 2.05/m/1H (DS 1 or DS 2); 2.45–2.95/m/6H (DS 1 and DS 2); 3.10/m/1H (DS 1 or DS 2); 3.25–3.50/m/2H (DS 1 and DS 2); 6.48/t/2H (DS 1 and DS 2); 6.60/t/2H (DS 1 and DS 2); 6.85–7.0/m/4H (DS 1 and DS 2) |
| P-10 | 0.89/t/3H; 1.65/m/4H; 1.94/m/2H; 2.78/t/2H; 3.30/t/2H; 3.64/t/1H; 6.45/d/1H; 6.89/m/2H |
| P-10.1 | 1.37/d/3H; 1.95/m/2H; 2.10/s/1H; 2.79/t/2H; 3.30/m/2H; 3.98/g/1H; 6.45/m/1H; 6.95/m/2H |
| P-11 | 0.95/t/3H; 1.90/m/2H; 4.20/m/1H; 7.40/d/1H; 7.53/t/1H; 7.72/t/1H; 7.81/d/1H; 8.08/d/1H; 8.13/d/1H |
| P-11.1 | 1.39/d/3H; 1.54/m/1H; 1.91/t/2H; 2.20/m/3H; 2.75/m/2H; 3.30/t/2H; 4.0/m/1H; 6.50/s/1H; 6.58/d/1H; 6.92/d/1H |
| P-12 | 0.89/t/3H; 1.60–1.72/m/2H; 2.65/t/2H; 2.98/t/2H; 3.74/m/1H; 6.75/d/1H; 7.08–7.15/m/2H; 8.57/s/1H |
| P-13.1 | 1.39/d/3H; 1.40–2.05/m/4H; 2.76/m/2H; 3.03/t/2H; 4.03/q/1H; 6.69/d/1H; 7.00/dd/1H; 7.08/s/1H |
| P-13.2 | 1.40/d/3H; 1.70–2.05/m/4H; 1.88/s/3H; 2.55–2.81/m/3H; 4.12/q/1H; 4.69/dt/1H, 7.09/d/1H; 7.18–7.26/m/2H |
| P-14.2 | 0.89/t/3H; 1.45–1.95/m/9H; 2.75/m/2H; 3.05/m/2H; 3.71/t/1H; 6.69/m/1H; 6.76/dd/1H; 7.05/d/1H |
| P-15.4 | 1.52/d/3H; 1.60/s/2H; 4.34/q/1H; 7.49/d/1H; 7.63/dd/1H; 7.79/dd/1H; 8.0/d/1H; 8.05/d/1H |
| P-15.20 | 1.52/d/3H; 4.40/q/1H; 7.02/m/2H; 7.22/d/1H; 7.35/d/2H; 7.40–7.50/m/2H; 7.78–8.09/m/2H |
| P-15.21 | 0.97/t/3H; 1.90/m/2H; 4.18/t/1H; 7.0–7.5/m/7H; 8.0/d/1H; 8.08/d/1H |
| P-16.1 | 1.52/d/3H; 1.72/s/2H; 4.40/q/1H; 7.57/d/1H; 7.70/m/1H; 7.82/dd/1H; 8.12/d/1H; 8.89/m/1H |
| P-17.1 | 1.50/d/3H; 4.36/q/1H; 7.40/m/1H; 7.72/dd/1H; 7.80/s/1H; 8.08/d/1H; 8.12/d/1H; 8.89/m/1H |
| P-18.1 | 1.50/d/3H; 1.70/s/2H; 4.37/q/1H; 7.39/m/1H; 7.60/dd/1H; 7.81/d/1H; |

TABLE 23-continued

| Example | $^1$H-NMR data (ppm/multiplicity/number of protons) |
|---|---|
| | 8.04/s/1H; 8.15/dd/2H; 8.90/m/1H |
| P-21.1 | 1.40/d/3H; 2.22/m/2H; 2.36/t/2H; 2.80/t/2H; 4.10/q/1H; 6.90/d/1H; 7.15–7.25/m/2H; 7.50/s/1H |
| P-21.2 | 0.90/t/3H; 1.70/t/2H; 2.25/m/2H; 2.38/m/2H; 2.80/t/2H; 3.80/m/1H; 6.90/s/1H; 7.10–7.22/m/2H; 7.29/s/1H |
| P-22.2 | 0.90/t/3H; 1.29/t/3H; 1.70/t/2H; 2.20–2.49/m/4H; 2.75/s/2H; 3.60–3.90/m/3H; 7.08/d/1H; 7.18/d/1H, 7.42/s/1H |

Examples F-1.1 to F-6.3: Formulation of compounds of the invention

Examples F-1.1 to F-1.3: Emulsifiable concentrates

| Constituents | F-1.1 | F-1.2 | F-1.3 |
|---|---|---|---|
| compound of the invention | 25% | 40% | 50% |
| calcium dodecylbenzene sulfonate | 5% | 8% | 6% |
| castor oil polyethylene glycol ether (36 moles of ethyleneoxy units) | 5% | — | — |
| tributylphenol polyethylene glycol ether (30 moles of ethyleneoxy units) | — | 12% | 4% |
| cyclohexanone | — | 15% | 20% |
| xylene mixture | 65% | 25% | 20% |

Emulsions of any desired concentration can be prepared from those emulsifiable concentrates by dilution with water.

Example F-2: Emulsifiable concentrate

| Constituents | F-2 |
|---|---|
| compound of the invention | 10% |
| octylphenol polyethylene glycol ether (4 to 5 moles of ethyleneoxy units) | 3% |
| calcium dodecylbenzene sulfonate | 3% |
| castor oil polyglycol ether (36 moles of ethyleneoxy units) | 4% |
| cyclohexanone | 30% |
| xylene mixture | 50% |

Emulsions of any desired concentration can be prepared from that emulsifiable concentrate by dilution with water.

Examples F-3.1 to F-3.4: Solutions

| Constituents | F-3.1 | F-3.2 | F-3.3 | F-3.4 |
|---|---|---|---|---|
| compound of the invention | 80% | 10% | 5% | 95% |
| propylene glycol monomethyl ether | 20% | — | — | — |
| polyethylene glycol (relative molecular weight: 400 atomic mass units) | — | 70% | — | — |
| N-methylpyrrolid-2-one | — | 20% | — | — |
| epoxidised coconut oil | — | — | 1% | 5% |
| petroleum fraction (boiling range: 160–190°) | — | — | 94% | — |

The solutions are suitable for use in the form of microdrops.

Examples F-4.1 to F-4.4: Granules

| Constituents | F-4.1 | F-4.2 | F-4.3 | F-4.4 |
|---|---|---|---|---|
| compound of the invention | 5% | 10% | 8% | 21% |
| kaolin | 94% | — | 79% | 54% |
| highly disperse silicic acid | 1% | — | 13% | 7% |
| at/apulgite | — | 90% | — | 18% |

The compound of the invention is dissolved in dichloromethane, the solution is sprayed onto the carrier and the solvent is then evaporated off in vacuo.

Examples F-5.1 and F-5.2: Dusts

| Constituents | F-5.1 | F-5.2 |
|---|---|---|
| compound of the invention | 2% | 5% |
| highly disperse silicic acid | 1% | 5% |
| talcum | 97% | — |
| kaolin | — | 90% |

Ready-for-use dusts are obtained by intimately mixing all the constituents.

Examples F-6.1 to F-6.3: Wettable powders

| Constituents | F-6.1 | F-6.2 | F-6.3 |
|---|---|---|---|
| compound of the invention | 25% | 50% | 75% |
| sodium lignosulfonate | 5% | 5% | — |
| sodium lauryl sulfate | 3% | — | 5% |
| sodium diisobutylnaphthalene sulfonate | — | 6% | 10% |
| octylphenol polyethylene glycol ether (7 to 8 moles of ethyleneoxy units) | — | 2% | — |
| highly disperse silicic acid | 5% | 10% | 10% |
| kaolin | 62% | 27% | — |

All the constituents are thoroughly mixed and the mixture is thoroughly ground in a suitable mill, affording a wettable powder that can be diluted with water to give suspensions of any desired concentration.

Examples B-1.1 to B-10: Biological activity of compounds of the invention

A. Microbicidal action

Example B-1.1: Systemic action against *Pythium ultimum* on *sugar beet*

Test method: Mycelium of *Pythium ultimum* is mixed with soil (500 ml of mycelium suspension to 10 liters of soil) and the mixture is introduced into 250 ml plastic trays. After incubation for 4 days at 10°, 10 seeds of the sugar beet plant to be tested are sown in each tray. On the following day, the trays are each watered with 50 ml of an aqueous spray solution (0,002 % active ingredient) comprising one of the compounds of the invention. After a 7-day incubation phase at 10° and a subsequent 4-day incubation phase at 22°, the activity of the active ingredient is evaluated on the basis of the number and appearance of the emerged plants.

Test result: Compounds of the invention exhibit good systemic activity against Pythium ultimum on sugar beet.

Example B-1.2: Systemic action against *Pythium ultimum* on maize

Test method: The test is carried out in a manner analogous to that described in Example B-1.1.

Test result: Compounds of the invention exhibit good systemic activity against Pythium ultimum on maize.

Example B-2: Action against *Puccinia graminis* on wheat a) Residual-protective action Test method: Wheat plants are sprayed to drip point 6 days after sowing with an aqueous spray mixture (0.02 % active ingredient) prepared from a wettable powder formulation of one of the compounds of the invention. After 24 hours the treated plants are infected with a uredospore suspension of the fungus. The plants are incubated for 48 hours (conditions: 95-100 % relative humidity at 20°) and then placed in a greenhouse at 22°. The development of rust pustules is assessed 12 days after infection in order to evaluate the activity of the active ingredient.

Test result: Compounds of the invention exhibit good residual-protective activity against Puccinia graminis on wheat, for example the compounds according to Examples P-1.5 and P-7.7 reduce fungal infestation to from 20 to 5% and the compound according to Example P-5.21 reduces fungal infestation to from 5 to 0%. Infected control plants not treated with the active ingredient, on the other hand, exhibit a fungal infestation of 100%.

b) Systemic action

Test method: Wheat plants are watered 5 days after sowing with an aqueous spray mixture (0.006% active ingredient, based on the volume of the soil) prepared from a wettable powder formulation comprising one of the compounds of the invention. Care is taken that the spray mixture does not come into contact with the parts of the plants above the soil. The treated plants are infected 48 hours later with a uredospore suspension of the fungus. After an incubation period of 48 hours (conditions: 95 to 100 percent relative humidity at 20°), the plants are placed in a greenhouse at 22°. The development of rust pustules is assessed 12 days after infection in order to evaluate the activity of the active ingredient.

Test result: Compounds of the invention exhibit good systemic activity against Puccinia graminis on wheat.

Example B-3: Action against *Phytophthora infestans* on *tomato plants* a) Residual-protective action

Test method: After a cultivation period of 3 weeks, tomato plants are sprayed to drip point with an aqueous spray mixture (0.02% active ingredient) prepared from a wettable powder formulation of one of the compounds of the invention. After 24 hours the treated plants are infected with a sporangia suspension of the fungus. 5 days after infection, during which time 90 to 100 percent relative humidity and a temperature of 20° are maintained, fungal infestation is evaluated in order to assess the activity of the active ingredient.

Test result: Compounds of the invention exhibit good residual-protective activity against Phytophthora infestans on tomato plants, for example the compounds according to Examples P-1.1.1 and P-7.8 reduce fungal infestation to from 20 to 0% and the compounds according to Examples P-1.1.2, P-5.1, P-5.18, P-5.2i and P-7.7 reduce fungal infestation to from 5 to 0%. Infected control plants not treated with the active ingredient, on the other hand, exhibit a fungal infestation of 100%.

b) Systemic action

Test method: After a cultivation period of 3 weeks, tomato plants are watered with an aqueous spray mixture (0.006% active ingredient, based on the volume of the soil) prepared from a wettable powder formulation of one of the compounds of the invention. Care is taken that the spray mixture does not come into contact with the parts of the plants above the soil. The plants are infected 48 hours later with a sporangia suspension of the fungus. 5 days after infection, during which time 90 to 100% humidity and a temperature of 20° are maintained, fungai infestation is assessed in order to evaluate the activity of the active ingredient.

Test result: Compounds of the invention exhibit good systemic activity against Phytophthora infestans on tomatoes.

Example B-4: Residual-protective action against *Cercospora arachidicola* on *groundnut plants*

Test method: Groundnut plants 10–15 cm in height are sprayed to drip point with an aqueous spray mixture (0.02% active ingredient) prepared from a wettable powder formulation of one of the compounds of the invention and infected 48 hours later with a conidia suspension of the fungus. The infected plants are incubated for 72 hours at 21° and high humidity and then placed in a greenhouse until the typical leaf specks occur. The activity of the active ingredient is evaluated 12 days after infection and is based on the number and size of the specks.

Test result: Compounds of the invention exhibit good residual-protective activity against Cercospora arachidicola on groundnut plants, for example the compounds according to Examples P-5.18 and P-7.8 reduce fungal infestation to from 20 to 0% and the compound according to Example P-7.7 reduces fungal infestation to from 5 to 0%. Infected control plants not treated with the active ingredient, on the other hand, exhibit a fungai infestation of 100%.

Example B-5: Action against *Plasmopara viticola* on vines a) Residual-protective action Test method: Vine seedlings in the 4- to 5-leaf stage are sprayed to drip point with an aqueous spray mixture (0.02% active ingredient) prepared from a wettable powder formulation of one of the compounds of the invention. After 24 hours the treated plants are infected with a sporangia suspension of the fungus. 6 days after infection, during which time 95 to 100% relative humidity and a temperature of 20° are maintained, fungal infestation is assessed in order to evaluate the activity of the active ingredient.

Test result: Compounds of the invention exhibit good preventive residual-protective activity against Plasmopara viticola on vines.

b) Residual-protective action

Test method: Vine seedlings in the 4- to 5-leaf stage are infected with a sporangia suspension of the fungus. After incubation for 24 hours in a humidity chamber (conditions: 95 to 100% relative humidity at 20°), the infected plants are sprayed to drip point with an aqueous spray mixture (0.02% active ingredient) prepared from a wettable powder formulation of one of the compounds of the invention. After the spray coating has dried, the treated plants are again placed in the humidity chamber. Fungal infestation is assessed 6 days after infection in order to evaluate the activity of the active ingredient.

Test result: Compounds of the invention exhibit good curative residual-protective activity against Plasmopara viticola on vines.

Example B-6: Action against *Pyricularia oryzae* on *rice plants* a) Residual-protective action

Test method: After a cultivation period of 2 weeks, rice plants are sprayed to drip point with an aqueous spray mixture (0.02% active ingredient) prepared from a wettable powder formulation of one of the compounds of the invention. After 48 hours the treated plants are infected with a conidia suspension of the fungus. 5 days after infection, during which time 95 to 100% relative humidity and a temperature of 22° are maintained, fungal infestation is assessed in order to evaluate the activity of the active ingredient.

Test result: Compounds of the invention exhibit good residual-protective activity against Pyricularia oryzae on rice.

b) Systemic action

Test method: 2-week-old rice plants are watered with an aqueous spray mixture (0.006% active ingredient, based on the volume of the soil) prepared from a wettable powder formulation of one of the compounds of the invention. Care is taken that the spray mixture does not come into contact with the parts of the plants above the soil. The pots are then filled with water so that the lowermost parts of the stems of the rice plants stand in water. After 96 hours, the treated plants are infected with a conidia suspension of the tungus. 5 days after infection, during which time 95 to 100% relative humidity and a temperature of 24° are maintained, fungal infestation is assessed in order to evaluate the activity of the active ingredient.

Test result: Compounds of the invention exhibit good systemic activity against Pyricularia oryzae on rice.

Example B-7: Residual-protective action against *Venturia inaequalis* on apples

Test method: Apple cuttings with 10 to 20 cm long fresh shoots are sprayed to drip point with an aqueous spray mixture (0.02% active ingredient) prepared from a wettable powder formulation of one of the compounds of the invention. The treated plants are infected 24 hours later with a conidia suspension of the fungus. The plants are then incubated for 5 days at 90 to 100% relative humidity and placed in a greenhouse for a further 10 days at 20 to 24°. Scab infestation is assessed 15 days after infection in order to evaluate the activity of the active ingredient.

Test result: Compounds of the invention exhibit good residual-protective activity against Venturia inaequalis on apples.

Example B-8: Action against *Erysiphe graminis* on barley a) Residual-protective action Test method: Barley plants about 8 cm in height are sprayed to drip point with an aqueous spray mixture (0.02% active ingredient) prepared from a wettable powder formulation of one of the compounds of the invention. The treated plants are dusted with conidia of the fungus after 3 to 4 hours. The infected plants are placed in a greenhouse at 22°. Fungal infestation is assessed 10 days after infection in order to evaluate the activity of the active ingredient.

Test result: Compounds of the invention exhibit good residual-protective activity against Erysiphe graminis on barley. For example, the compounds according to Examples P-1.1.1, P-1.8 and P-5.1 reduce fungai infestation to from 20 to 0% and the compounds according to Examples P-1.1.2, P-5.5 and P-5.21 reduce fungal infestation to from 5 to 0%. Infected control plants not treated with the active ingredient, on the other hand, exhibit a fungai infestation of 100%.

b) Systemic action

Test method: An aqueous spray mixture (0.002% active ingredient, based on the volume of the soil) prepared from a wettable powder formulation of one of the compounds of the invention is used to water barley plants about 8 cm in height. Care is taken that the spray mixture does not come into contact with the parts of the plants above the soil. The treated plants are dusted 48 hours later with conidia of the fungus. The infected plants are then placed in a greenhouse at 22°. Fungai infestation is assessed 10 days after infection in order to evaluate the activity of the active ingredient.

Test result: Compounds of the invention exhibit good systemic activity against Erysiphe graminis on barley.

Example B-9: Action against Podosphaera leucotricha on apple shoots Residual-protective action Apple cuttings with approximately 15 cm long fresh shoots are sprayed with a spray mixture (0.06% active ingredient). The treated plants are infected 24 hours later with a conidia suspension of the fungus and placed in a humidity chamber at 70% relative humidity and 20° C. Fungal infestation is evaluated 12 days after infection.

Test result: Compounds of the invention exhibit good activity against Podosphaera on apple shoots.

Example B-10: Action against *Tetranychus urticae* on beans

Test method: Young bean plants are populated with a mixed population of Tetranychus urticae and sprayed to drip point one day later with an aqueous emulsion (0.04% active ingredient) prepared from a wettable powder formulation of one of the compounds of the invention. The plants are then incubated for 6 days at 25°. The activity of the active ingredient is then evaluated on the basis of a count of the pests. The dead eggs, dead larvae and dead adults on the treated plants are counted and the corresponding figures are determined in analogous manner for the control plants not treated with the active ingredient. The percentage by which the pest population on the treated plants has been reduced (percentage activity of the active ingredient) is calculated from the pairs of values for the treated and untreated plants.

Test result: Compounds of the invention exhibit good activity against Tetranychus urticae on beans.

B. Acaricidal/insecticidal action

Example B-11: Action against *Tetranychus cinnabafinus* on *dwarf beans*

Test methods (dilution series): Dwarf beans in the 2-leaf stage are populated with a mixed population (eggs, larvae/nymphs and adults) of an OP-tolerant strain of Tetranychus cinnabarinus. The compound of the invention is applied to the plants 24 hours later in concentrations of 200, 100 and 50 me/1 in an automatic spraying chamber (the compound is formulated and diluted with water to the appropriate concentration). The activity of the active ingredient is evaluated 2 and 7 days after application on the basis of a count of the pests. The dead eggs, dead larvae/nymphs and dead adults on the treated plants (treated with active ingredient in a particular concentration) are counted and the corresponding figures are determined in analogous manner for the control plants not treated with the active ingredient. The percentage by which the pest population on the treated plants has been reduced (percentage activity of the active ingredient) is calculated from the pairs of values for the treated (with active ingredient in the particular concentration) and untreated plants.

Test result: Compounds of the invention exhibit good activity against Tetranychus cinnabarinus on dwarf beans.

B-12: Action against Nilaparvata lugens

Rice plants are sprayed with an aqueous emulsion comprising 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Test result: Compounds of the invention exhibit good activity against Nilaparvata lugens.

B-13: Ovicidal/larvicidal action against Heliothis virescens

Egg deposits of Hellothis virescens on cotton are sprayed with an aqueous emulsion comprising 400 ppm of the test compound. 8 days later, the percentage of eggs which have hatched and the survival rate of the caterpillars are evaluated in comparison with untreated controls (percentage reduction in the population).

Test result: Compounds of the invention exhibit good activity against Hellothis virescens.

B-14: Action against Plutella xylostella caterpillars

Young cabbage plants are sprayed with an aqueous emulsion comprising 400 ppm of the test compound. After the spray coating has dried, the cabbage plants are populated with 10 Plutella xylostella caterpillars in the third stage and placed in a plastics container. Evaluation is made 3 days later. The percentage reduction in the population and the percentage reduction in feeding damage (% activity) is determined by comparing the number of dead caterpillars and the feeding damage on the treated plants with that on untreated plants.

Test result: Compounds of the invention, especially the compounds P-1.1.1 and P-1.1.2, exhibit good activity against Plutella xylostella.

What is claimed is:

1. A compound of the formula

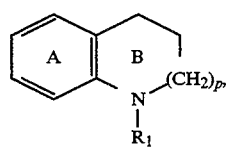

(I)

wherein one of the (p+6) substitutable ring carbon atoms of the two rings A and B is substituted by a group of formula Ia

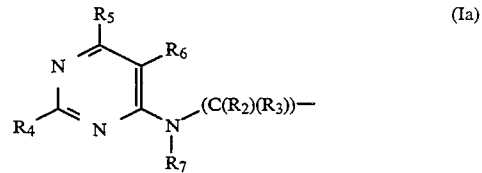

(Ia)

and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, di-substituted, any substituents present at the mentioned (p+5) substitutable ring carbon atoms of the two rings A and B being selected from the group consisting of halogen, $C_1$-$C_8$alkyl, halo-$C_1$-$C_8$alkyl, $C_1$-$C_4$alkoxy-$C_1$-$C_4$alkyl, $C_3$-$C_8$cycloalkyl, $C_1$-$C_8$alkoxy, halo-$C_1$-$C_8$alkoxy, $C_3$-$C_8$cycloalkoxy, $C_1$-$C_8$alkylthio, halo-$C_1$-$C_8$alkylthio, cyano, nitro, phenyl, phenoxy and phenylthio, the phenyl groups in phenyl, phenoxy and phenylthio being unsubstituted or substituted by one, two or three substituents selected from the group consisting of halogen, $C_1$-$C_4$alkyl and $C_1$-$C_4$alkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

$R_1$ is hydrogen, $C_1$-$C_8$alkyl, $C_3$-$C_8$cycloalkyl, benzyl, $C_1$-$C_8$alkanoyl that is unsubstituted or substituted by halogen or by $C_1$-$C_4$alkoxy, benzoyl the phenyl group of which is unsubstituted or substituted by one or two substituents selected from the group consisting of halogen, $C_1$-$C_4$alkyl, nitro and cyano; $C_1$-$C_8$alkanesulfonyl, halo-$C_1$-$C_8$alkanesulfonyl, cyano-$C_1$-$C_8$alkanesulfonyl or phenylsulfonyl the phenyl group of which is unsubstituted or substituted by one or two substituents selected from the group consisting of halogen, $C_1$-$C_4$alkyl, nitro and cyano;

$R_2$ and $R_3$, independently of one another, are hydrogen, $C_1$-$C_8$halo-$C_1$-$C_8$alkyl, $C_1$-$C_4$alkoxy-$C_1$-$C_4$alkyl or $C_3$-$C_8$cycloalkyl;

$R_4$ is hydrogen, $C_1$-$C_8$alkyl, $C_1$-$C_8$alkoxy or $C_1$-$C_8$alkylthio;

$R_5$ is hydrogen, $C_1$-$C_8$alkyl, halo-$C_1$-$C_8$alkyl, $C_1$-$C_4$alkoxy-$C_1$-$C_4$alkyl, $C_1$-$C_4$alkylthio-$C_1$-$C_4$alkyl, $C_1$-$C_4$alkanesulfinyl-$C_1$-$C_4$alkyl, $C_1$-$C_4$alkanesulfonyl-$C_1$-$C_4$alkyl, $C_2$-$C_8$alkenyl, halo-$C_2$-$C_8$alkenyl, $C_2$-$C_8$alkynyl, $C_3$-$C_8$cycloalkyl, $C_1$-$C_8$alkylthio or halogen;

$R_6$ is hydrogen, hydroxy, $C_1$-$C_8$alkyl, halo-$C_1$-$C_8$alkyl, $C_1$-$C_4$alkoxy-$C_1$-$C_4$alkyl, $C_1$-$C_8$alkoxy, $C_1$-$C_8$alkylthio, $C_1$-$C_8$alkanesulfinyl, $C_1$-$C_8$alkanesulfonyl, halogen, nitro, cyano, amino, a group of the formula N(H)$R_8$(Ib), a group of the formula N($R_8$)$R_9$ (Ic) or a group of the formula N=C($R_9$)$R_{10}$(Id);

$R_7$ is hydrogen, $C_1$-$C_8$alkyl, benzyl, $C_1$-$C_8$alkanoyl, phenylcarbonyl the phenyl group of which is unsubstituted or substituted by one, two or three substituents selected from the group consisting of halogen and $C_1$-$C_4$alkyl; $C_1$-$C_8$alkylthio, halo- $C_1$–$C_8$alkylthio, cyano-$C_1$–$C_8$alkylthio, phenylthio or benzylthio, the phenyl groups in phenylthio and benzylthio being unsubstituted or substituted by one or two substituents selected from the group consisting of halogen, $C_1$–$C_4$alkyl, nitro and cyano;

$R_8$ is $C_1$–$C_8$alkyl, benzyl, $C_1$–$C_8$alkanoyl, phenylcarbonyl the phenyl group of which is unsubstituted or substituted by one, two or three substituents selected from the group consisting of halogen and $C_1$–$C_4$alkyl; $C_1$–$C_8$alkylthio, halo-$C_1$–$C_8$alkylthio, cyano-$C_1$–$C_8$alkylthio, phenylthio or benzylthio, the phenyl groups in phenylthio and benzylthio being unsubstituted or substituted by one or two substituents selected from the group consisting of halogen, $C_1$–$C_4$alkyl, nitro and cyano;

$R_9$ is $C_1$–$C_8$alkyl;

$R_{10}$ is hydrogen or $C_1$–$C_8$alkyl; and p is 1 or 2;

or, where appropriate, a tautomer thereof, in each case in free form or in the form of a salt.

2. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, any substituents present at the mentioned (p+5) substitutable ring carbon atoms of the two rings A and B being selected from the group consisting of halogen, $C_1$–$C_4$alkyl, halo-$C_1$–$C_4$alkyl having 1, 2 or 3 halogen atoms, $C_1$–$C_2$alkoxy-$C_1$–$C_4$alkyl, $C_3$–$C_6$cycloalkyl, $C_1$–$C_4$alkoxy, halo-$C_1$–$C_4$alkoxy having 1, 2 or 3 halogen atoms, $C_3$–$C_7$cycloalkoxy, $C_1$–$C_4$alkylthio, halo-$C_1$–$C_4$alkylthio having 1, 2 or 3 halogen atoms, cyano, nitro, phenyl, phenoxy and phenylthio, the phenyl groups in phenyl, phenoxy and phenylthio being unsubstituted or substituted by one, two or three substituents selected from the group consisting of halogen, $C_1$–$C_2$alkyl and $C_1$–$C_2$alkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

$R_1$ is hydrogen, $C_1$–$C_4$alkyl, $C_3$–$C_7$cycloalkyl, benzyl, $C_1$–$C_4$alkanoyl that is unsubstituted or substituted by halogen or by $C_1$–$C_2$alkoxy, benzoyl the phenyl group of which is unsubstituted or substituted by one or two substituents selected from the group consisting of halogen, $C_1$–$C_2$alkyl, nitro and cyano; $C_1$–$C_4$alkanesulfonyl, halo-$C_1$–$C_4$alkanesulfonyl having 1, 2 or 3 halogen atoms, cyano-$C_1$–$C_4$alkanesulfonyl or phenylsulfonyl the phenyl group of which is unsubstituted or substituted by one or two substituents selected from the group consisting of halogen, $C_1$–$C_2$alkyl, nitro and cyano;

$R_2$ and $R_3$, independently of one another, are hydrogen, $C_1$–$C_4$alkyl, halo-$C_1$–$C_4$alkyl having 1, 2 or 3 halogen atoms, $C_1$–$C_2$alkoxy-$C_1$–$C_4$alkyl or $C_3$–$C_7$cycloalkyl;

$R_4$ is hydrogen, $C_1$–$C_4$alkyl, $C_1$–$C_4$alkoxy or $C_1$–$C_4$alkylthio;

$R_5$ is hydrogen, $C_1$–$C_4$alkyl, halo-$C_1$–$C_4$alkyl having 1, 2 or 3 halogen atoms, $C_1$–$C_2$alkoxy-$C_1$–$C_4$alkyl, $C_1$–$C_2$alkylthio-$C_1$–$C_4$alkyl, $C_1$–$C_2$alkanesulfinyl-$C_1$–$C_4$alkyl, $C_1$–$C_2$alkanesulfonyl-$C_1$–$C_4$alkyl, $C_2$–$C_4$alkenyl, halo-$C_2$–$C_4$alkenyl having 1, 2 or 3 halogen atoms, $C_2$–$C_4$alkynyl, $C_3$–$C_7$cycloalkyl, $C_1$–$C_4$alkylthio or halogen;

$R_6$ is hydrogen, hydroxy, $C_1$–$C_4$alkyl, halo-$C_1$–$C_4$alkyl having 1, 2 or 3 halogen atoms, $C_1$–$C_2$alkoxy-$C_1$–$C_4$alkyl, $C_1$–$C_4$alkoxy, $C_1$–$C_4$alkylthio, $C_1$–$C_4$alkanesulfinyl, $C_1$–$C_2$alkanesulfonyl, halogen, nitro, cyano, amino, a group of the formula N(H)$R_8$(Ib), a group of the formula N($R_8$)$R_9$ (Ic) or a group of the formula N=C($R_9$)$R_{10}$ (Id);

$R_7$ is hydrogen, $C_1$–$C_4$alkyl, benzyl, $C_1$–$C_4$alkanoyl, phenylcarbonyl the phenyl group of which is unsubstituted or substituted by one, two or three substituents selected from the group consisting of halogen and $C_1$–$C_2$alkyl; $C_1$–$C_4$alkylthio, halo-$C_1$–$C_4$alkylthio having 1, 2 or 3 halogen atoms, cyano-$C_1$–$C_4$alkylthio, phenylthio or benzylthio, the phenyl groups in phenylthio and benzylthio being unsubstituted or substituted by one or two substituents selected from the group consisting of halogen, $C_1$–$C_2$alkyl, nitro and cyano;

$R_8$ is $C_1$–$C_4$alkyl, benzyl, $C_1$–$C_4$alkanoyl, phenylcarbonyl the phenyl group of which is unsubstituted or substituted by one, two or three substituents selected from the group consisting of halogen and $C_1$–$C_2$alkyl $C_1$–$C_4$alkylthio, halo-$C_1$–$C_4$alkylthio having 1, 2 or 3 halogen atoms, cyano-$C_1$–$C_4$alkylthio, phenylthio or benzylthio, the phenyl groups in phenylthio and benzylthio being unsubstituted or substituted by one or two substituents selected from the group consisting of halogen, $C_1$–$C_2$alkyl, nitro and cyano;

$R_9$ is $C_1$–$C_4$alkyl;

$R_{10}$ is hydrogen or $C_1$–$C_4$alkyl; and p is 1 or 2;

or, where appropriate, a tautomer thereof, in each case in free form or in the form of a salt.

3. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$–$C_4$alkyl, halo-$C_1$–$C_4$alkyl having 1, 2 or 3 halogen atoms, $C_1$–$C_2$alkoxy-$C_1$–$C_4$alkyl, $C_3$–$C_6$cycloalkyl, $C_1$–$C_4$alkoxy, halo-$C_1$–$C_4$alkoxy having 1, 2 or 3 halogen atoms, $C_3$–$C_7$cycloalkoxy, $C_1$–$C_4$alkylthio, halo-$C_1$–$C_4$alkylthio having 1, 2 or 3 halogen atoms, cyano, nitro, phenyl, phenoxy and phenylthio, the phenyl groups in phenyl, phenoxy and phenylthio being unsubstituted or substituted by one, two or three substituents selected from the group consisting of halogen, $C_1$-$C_2$alkyl and $C_1$-$C_2$alkoxy, with the proviso that not more than one of any substituents present at the mentioned (p+5) substitutable ring carbon atoms of the two rings A and B is phenyl that is unsubstituted or substituted as mentioned above, phenoxy that is unsubstituted or substituted as mentioned above or phenylthio that is unsubstituted or substituted as mentioned above; wherein:

$R_1$ is hydrogen, $C_1$-$C_4$alkyl, $C_3$-$C_7$cycloalkyl, benzyl, $C_1$-$C_4$alkanoyl that is unsubstituted or substituted by halogen or by $C_1$-$C_2$alkoxy, benzoyl the phenyl group of which is unsubstituted or substituted by one or two substituents selected from the group consisting of halogen, $C_1$-$C_2$alkyl, nitro and cyano; $C_1$-$C_4$alkanesulfonyl, halo-$C_1$-$C_4$alkanesulfonyl having 1, 2 or 3 halogen atoms, cyan-$C_1$-$C_4$alkanesulfonyl or phenylsulfonyl the phenyl group of which is unsubstituted or substituted by one or two substituents selected from the group consisting of halogen, $C_1$-$C_2$alkyl, nitro and cyano;

$R_2$ and $R_3$, independently of one another, are hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl or $C_3$-$C_7$cycloalkyl;

$R_4$ is hydrogen, $C_1$-$C_4$alkyl, $C_1$-$C_4$alkoxy or $C_1$-$C_4$alkylthio;

$R_5$ is hydrogen, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_2$alkylthio-$C_1$-$C_4$alkyl, $C_1$-$C_2$alkanesulfinyl-$C_1$-$C_4$alkyl, $C_1$-$C_2$alkanesulfonyl-$C_1$-$C_4$alkyl, $C_2$-$C_4$alkenyl, halo-$C_2$-$C_4$alkenyl having 1, 2 or 3 halogen atoms, $C_2$-$C_4$alkynyl, $C_3$-$C_7$cycloalkyl, $C_1$-$C_4$alkylthio or halogen;

$R_6$ is hydrogen, hydroxy, $C_1$-$C_4$alkyl, halo-$C_1$-$C_4$alkyl having 1, 2 or 3 halogen atoms, $C_1$-$C_2$alkoxy-$C_1$-$C_4$alkyl, $C_1$-$C_4$alkoxy, $C_1$-$C_4$alkylthio, $C_1$-$C_4$alkanesulfinyl, $C_1$-$C_2$alkanesulfonyl, halogen, nitro, cyano, amino, a group of the formula $N(H)R_8$(Ib), a group of the formula $N(R_8)R_9$(Ic) or a group of the formula $N=C(R_9)R_{10}$(Id);

$R_7$ is hydrogen, $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl, $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$-$C_2$alkyl, nitro and cyano;

$R_8$ is $C_1$-$C_4$alkyl, benzyl, $C_1$-$C_4$alkanoyl, phenylcarbonyl the phenyl group of which is unsubstituted or substituted by one, two or three substituents selected from the group consisting of halogen and $C_1$-$C_2$alkyl, $C_1$-$C_4$alkylthio, halo-$C_1$-$C_4$alkylthio having 1, 2 or 3 halogen atoms, cyano-$C_1$-$C_4$alkylthio, phenylthio or benzylthio, the phenyl groups in phenylthio and benzylthio being unsubstituted or substituted by one or two substituents selected from the group consisting of halogen, $C_1$-$C_2$alkyl, nitro and cyano;

$R_9$ is $C_1$-$C_4$alkyl;

$R_{10}$ is hydrogen or $C_1$-$C_4$alkyl; and p is 1 or 2;

or, where appropriate, a tautomer thereof, in each case in free form or in the form of a salt.

4. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$-$C_4$alkyl and $C_1$-$C_4$alkoxy, wherein:

$R_1$ is hydrogen, $C_1$-$C_4$alkyl or $C_1$-$C_4$alkanoyl;

$R_2$ and $R_3$, independently of one another, are hydrogen or $C_1$-$C_4$alkyl;

$R_4$ is hydrogen or $C_1$-$C_4$alkyl;

$R_5$ is $C_1$-$C_4$alkyl, halo-$C_1$-$C_4$alkyl having 1, 2 or 3 halogen atoms, $C_2$-$C_4$alkynyl, $C_3$-$C_4$cycloalkyl or $C_1$-$C_4$alkylthio;

$R_6$ is $C_1$-$C_4$alkylthio, halogen, nitro or amino;

$R_7$ is hydrogen or $C_1$-$C_4$alkyl; and p is 1 or 2;

or, where appropriate, a tautomer thereof, in each case in free form or in the form of a salt.

5. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, with the proviso that when p is 1 the group Ia is bonded in the 2-, 3-, 6- or 7-position of the bicyclic ring system of formula I formed from the two rings A and B, with the further proviso that when p is 2 the group Ia is bonded in the 2-, 3-, 7- or 8-position of the bicyclic ring system of formula I formed from the two rings A and B, any substituents present at the mentioned (p+5) substitutable ring carbon atoms of the two rings A and B being selected from the group consisting of halogen, $C_1$-$C_4$alkyl and $C_1$-$C_4$alkoxy; wherein:

$R_1$ is hydrogen, $C_1$-$C_4$alkyl or $C_1$-$C_4$alkanoyl;

$R_2$ and $R_3$, independently of one another, are hydrogen or $C_1$-$C_4$alkyl;

$R_4$ is hydrogen;

$R_5$ is $C_1$-$C_4$alkyl;

$R_6$ is halogen;

$R_7$ is hydrogen; and p is 1 or 2;

in free form or in the form of a salt.

6. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, with the proviso that the group Ia is bonded in the 2-, 3-, 6- or 7-position of the bicyclic ring system of formula I formed from the two rings A and B, any substituents present at the mentioned (p+5) substitutable ring carbon atoms of the two rings A and B being selected from the group consisting of halogen, $C_1$–$C_4$alkyl and $C_1$–$C_4$alkoxy; wherein:

$R_1$ is hydrogen or $C_1$–$C_4$alkanoyl;
$R_2$ is hydrogen;
$R_3$ is $C_1$–$C_4$alkyl;
$R_4$ is hydrogen;
$R_5$ is $C_1$–$C_4$alkyl;
$R_6$ is halogen;
$R_7$ is hydrogen; and
p is 1;

in free form or in the form of a salt.

7. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one or, independently of one another, two or three of those other (p+5) substitutable ring carbon atoms of the two rings A and B is(are) monosubstituted or, in the case of the saturated ring carbon atoms of the ring B, mono- or, independently of one another, disubstituted, with the proviso that the group Ia is bonded in the 6- or 7-position of the bicyclic ring system of formula I formed from the two rings A and B, any substituents present at the mentioned (p+5) substitutable ring carbon atoms of the two rings A and B being selected from the group consisting of $C_1$–$C_2$alkyl; wherein:

$R_1$ is hydrogen or $C_1$–$C_2$alkanoyl;
$R_2$ is hydrogen;
$R_3$ is $C_1$–$C_2$alkyl;
$R_4$ is hydrogen;
$R_5$ is $C_1$–$C_2$alkyl;
$R_6$ is chlorine;
$R_7$ is hydrogen; and
p is 1;

in free form or in the form of a salt.

8. A compound according to claim 1 of formula I wherein one of the (p+6) substitutable ring carbon atoms of the two rings A and B is substituted by a group Ia and the other (p+5) substitutable ring carbon atoms of the two rings A and B are unsubstituted or one of those other (p+5) substitutable ring carbon atoms of the two rings A and B, especially the ring carbon atom in the 2-position of the bicyclic ring system of formula I formed from the two rings A and B, is monosubstituted by $C_1$–$C_2$alkyl, with the proviso that the group Ia is bonded in the 7-position of the bicyclic ring system of formula I formed from the two rings A and B; wherein:

$R_1$ is hydrogen or $C_1$–$C_2$alkanoyl;
$R_2$ is hydrogen;
$R_3$ is $C_1$–$C_2$alkyl;
$R_4$ is hydrogen;
$R_5$ is $C_1$–$C_2$alkyl;
$R_6$ is chlorine;
$R_7$ is hydrogen; and
p is 1;

in free form or in the form of a salt.

9. A compound according to claim 1 of formula I, selected from the group of compounds consisting of
(a) 2-[1-(5-chloro-6-ethyl-pyrimidin-4-ylamino)prop-1-yl]-1,2,3,4-tetrahydro-quinoline,
(b) 2-[1-(5-chloro-6-ethyl-pyrimidin-4-ylamino)ethyl]-1,2,3,4-tetrahydro-quinoline (diastereoisomer 1),
(c) 2-[1-(5-chloro-6-ethyl-pyrimidin-4-ylamino)ethyl]-1,2,3,4-tetrahydro-quinoline (diastereoisomer 2),
(d) 2-[1-(5-chloro-6-ethyl-pyrimidin-4-ylamino)ethyl]-6-methoxy-1,2,3,4-tetrahydro-quinoline,
(e) 6-[1-(5-chloro-6-ethyl-pyrimidin-4-ylamino).ethyl]-1,2,3,4-tetrahydro-quinoline,
(f) 7-[1-(5-chloro-6-ethyl-pyrimidin-4-ylamino)ethyl]-1,2,3,4-tetrahydro-quinoline,
(g) a mixture of 6-[1-(5-chloro-6-ethyl-pyrimidin-4-ylamino)ethyl]-1,2,3,4-tetrahydro-quinoline and 7-[1-(5-chloro-6-ethyl-pyrimidin-4-ylamino)ethyl]-1,2,3,4-tetrahydro-quinoline,
(h) a mixture of 1-acetyl-6-[1-(5-chloro-6-ethyl-pyrimidin-4-ylamino)ethyl]-1,2,3,4-tetrahydro-quinoline and 1-acetyl-7-[1-(5-chloro-6-ethyl-pyrimidin-4-ylamino)ethyl]-1,2,3,4-tetrahydro-quinoline,
(i) a mixture of 1-acetyl-6-[1-(5-chloro-6-ethyl-pyrimidin-4-ylamino)prop-1-yl]-2-methyl-1,2,3,4-tetrahydro-quinoline and 1-acetyl-7-[1-(5-chloro-6-ethyl-pyrimidin-4-ylamino)prop-1-yl]-2-methyl-1,2,3,4-retrahydro-quinoline,
(j) a mixture of 6-[1-(5-chloro-6-ethyl-pyrimidin-4-ylamino)prop-1-yl]-2-methyl-1,2,3,4-tetrahydro-quinoline and 7-[1-(5-chloro-6-ethyl-pyrimidin-4-ylamino )prop-1-yl]-2-methyl-1,2,3,4-tetrahydro-quinoline,
(k) 1-acetyl-8-[1-(5-chloro-6-ethyl-pyrimidin-4-ylamino)ethyl]-2,3,4,5-tetrahydro-1H-benzo[b]azepine, and
(l) 1-acetyl-8-[1-(5-chloro-6-ethyl-pyrimidin-4-ylamino)prop-1-yl ]-2,3,4,5-tetrahydro-1H-benzo[b]azepine, in each case in free form or in the form of a salt.

10. A composition for protecting plants against attack by phytopathogenic microorganisms and/or pests of the order Acarina and the class Insecta, which comprises at least one compound of the formula I according to claim 1 or, where appropriate, a tautomer thereof, in each case in free form or in the form of an agrochemically acceptable salt, as an active ingredient, and at least one adjuvant.

11. A composition according to claim 10 for protecting plants against attack by phytopathogenic microorganisms and/or pests of the order Acarina and the class Insecta.

12. A method of protecting plants against attack by phytopathogenic microorganisms and/or pests of the order Acarina and the class Insecta, which comprises applying as active ingredient an effective amount of a compound of the formula I according to claim 1 or, where appropriate, a tautomer thereof, in each case in free form or in the form of an agrochemically acceptable salt, to the plants to parts of the plants and/or to the locus of the plants.

13. A method according to claim 12 of protecting plants against attack by phytopathogenic microorganisms and/or pests of the order Acarina and the class Insecta.

* * * * *